United States Patent
Hollowell et al.

(10) Patent No.: US 8,961,553 B2
(45) Date of Patent: Feb. 24, 2015

(54) MATERIAL CONTROL DEVICE FOR INSERTING MATERIAL INTO A TARGETED ANATOMICAL REGION

(75) Inventors: Dan R. Hollowell, Longmont, CO (US); Richard W. Layne, Denver, CO (US); Jason C. Morton, Golden, CO (US)

(73) Assignee: Crosstrees Medical, Inc., Boulder, CO (US)

( * ) Notice: Subject to any disclaimer, the term of this patent is extended or adjusted under 35 U.S.C. 154(b) by 871 days.

(21) Appl. No.: 12/677,933

(22) PCT Filed: Sep. 15, 2008

(86) PCT No.: PCT/US2008/076463
§ 371 (c)(1),
(2), (4) Date: Oct. 29, 2010

(87) PCT Pub. No.: WO2009/036466
PCT Pub. Date: Mar. 19, 2009

(65) Prior Publication Data
US 2011/0054416 A1    Mar. 3, 2011

Related U.S. Application Data

(60) Provisional application No. 60/993,751, filed on Sep. 14, 2007.

(51) Int. Cl.
*A61M 25/00* (2006.01)
*A61B 17/70* (2006.01)
*A61B 17/88* (2006.01)

(52) U.S. Cl.
CPC ......... *A61B 17/7098* (2013.01); *A61B 17/8811* (2013.01); *A61B 17/8855* (2013.01)
USPC .......................... 606/192; 606/86 R; 604/264

(58) Field of Classification Search
USPC .......................... 606/86 R, 92, 192; 604/264
See application file for complete search history.

(56) References Cited

U.S. PATENT DOCUMENTS 4,625,722 A   12/1986   Murray
4,969,888 A   11/1990   Scholten et al.
(Continued)

FOREIGN PATENT DOCUMENTS

EP   1 495 729 A1   1/2005
EP   1 495 730 A1   1/2005
(Continued)

OTHER PUBLICATIONS

International Search Report and Written Opinion for International Application PCT/US06/61207, mailed Oct. 5, 2007.
(Continued)

*Primary Examiner* — Theodore Stigell
*Assistant Examiner* — Amber Stiles

(57) ABSTRACT

An extractable device is used to insert a flowable material into a vertebral body. The device comprises a filling member and a flowable material. The filling member is made of a flexible wall which includes a holding portion and an injection port via which the flowable material is injected into the holding portion after insertion into the vertebral body. The holding portion is provided with an opening which is releasably closed by a closure device so as to make the opening substantially resistant to the passage of material there through. Once the flowable material in the holding portion increases in viscosity, the closure device is released, thereby enabling the filling member to be extracted from the vertebral body so as to leave only the material in the vertebral body. The flowable material should be a material capable of setting to a hardened condition.

20 Claims, 33 Drawing Sheets

(56) References Cited

U.S. PATENT DOCUMENTS

| | | | |
|---|---|---|---|
| 4,983,168 A | 1/1991 | Moorehead | |
| 5,017,175 A | 5/1991 | Klusmire | |
| 5,054,492 A | 10/1991 | Scribner et al. | |
| 5,108,404 A | 4/1992 | Scholten et al. | |
| 5,489,307 A | 2/1996 | Kuslich | |
| 5,549,679 A | 8/1996 | Kuslich | |
| 5,632,275 A | 5/1997 | Browne et al. | |
| 5,744,958 A | 4/1998 | Werne | |
| 5,782,764 A | 7/1998 | Werne | |
| 5,827,289 A | 10/1998 | Reiley et al. | |
| 5,972,015 A | 10/1999 | Scribner et al. | |
| 5,976,186 A | 11/1999 | Bao et al. | |
| 6,048,346 A | 4/2000 | Reiley et al. | |
| 6,053,904 A | 4/2000 | Scribner et al. | |
| 6,066,154 A | 5/2000 | Reiley et al. | |
| 6,146,422 A | 11/2000 | Lawson | |
| 6,235,043 B1 | 5/2001 | Reiley et al. | |
| 6,241,734 B1 | 6/2001 | Scribner et al. | |
| 6,245,107 B1 | 6/2001 | Ferree | |
| 6,248,110 B1* | 6/2001 | Reiley et al. | 606/93 |
| 6,355,032 B1 | 3/2002 | Hovda et al. | |
| 6,402,784 B1 | 6/2002 | Wardlaw | |
| 6,440,138 B1 | 8/2002 | Reiley et al. | |
| 6,443,988 B2 | 9/2002 | Felt et al. | |
| 6,468,279 B1 | 10/2002 | Reo | |
| 6,488,710 B2 | 12/2002 | Besselink | |
| 6,508,839 B1 | 1/2003 | Lambrecht et al. | |
| 6,533,817 B1 | 3/2003 | Norton et al. | |
| 6,558,390 B2 | 5/2003 | Cragg | |
| 6,575,919 B1 | 6/2003 | Reiley et al. | |
| 6,602,291 B1 | 8/2003 | Ray et al. | |
| 6,607,544 B1 | 8/2003 | Boucher et al. | |
| 6,632,235 B2 | 10/2003 | Weikel et al. | |
| 6,641,587 B2 | 11/2003 | Scribner et al. | |
| 6,645,213 B2 | 11/2003 | Scribner et al. | |
| 6,676,665 B2 | 1/2004 | Foley et al. | |
| 6,706,069 B2* | 3/2004 | Berger | 623/17.12 |
| 6,712,819 B2 | 3/2004 | Zucherman et al. | |
| 6,716,216 B1 | 4/2004 | Boucher et al. | |
| 6,719,773 B1* | 4/2004 | Boucher et al. | 606/192 |
| 6,726,691 B2 | 4/2004 | Osorio et al. | |
| 6,740,093 B2 | 5/2004 | Hochschuler et al. | |
| 6,923,813 B2 | 8/2005 | Phillips et al. | |
| 6,932,843 B2 | 8/2005 | Smith et al. | |
| 6,960,215 B2 | 11/2005 | Olson, Jr. et al. | |
| 6,979,341 B2 | 12/2005 | Scribner et al. | |
| 7,044,954 B2 | 5/2006 | Reiley et al. | |
| 7,081,122 B1 | 7/2006 | Reiley et al. | |
| 7,097,648 B1 | 8/2006 | Globerman et al. | |
| 7,153,306 B2 | 12/2006 | Ralph et al. | |
| 7,166,110 B2* | 1/2007 | Yundt | 606/86 A |
| 7,166,121 B2 | 1/2007 | Reiley et al. | |
| 7,175,627 B2 | 2/2007 | Lin et al. | |
| 7,175,628 B2 | 2/2007 | Lin et al. | |
| 7,175,629 B2 | 2/2007 | Lin et al. | |
| 7,226,481 B2 | 6/2007 | Kuslich | |
| 7,241,303 B2* | 7/2007 | Reiss et al. | 606/192 |
| 7,261,720 B2 | 8/2007 | Stevens et al. | |
| 7,465,318 B2 | 12/2008 | Sennett et al. | |
| 7,749,230 B2* | 7/2010 | Yuan et al. | 606/86 R |
| 7,993,343 B2* | 8/2011 | Lin et al. | 606/86 R |
| 7,993,345 B2 | 8/2011 | Yuan et al. | |
| 8,007,500 B2 | 8/2011 | Lin et al. | |
| 2002/0026195 A1 | 2/2002 | Layne et al. | |
| 2002/0156482 A1 | 10/2002 | Scribner et al. | |
| 2003/0050644 A1 | 3/2003 | Boucher et al. | |
| 2004/0006347 A1 | 1/2004 | Sproul | |
| 2004/0024410 A1 | 2/2004 | Olson, Jr. et al. | |
| 2004/0059417 A1 | 3/2004 | Smith et al. | |
| 2004/0073308 A1 | 4/2004 | Kuslich et al. | |
| 2004/0102774 A1 | 5/2004 | Trieu | |
| 2004/0106999 A1 | 6/2004 | Mathews | |
| 2004/0122455 A1 | 6/2004 | Lin | |
| 2004/0186481 A1 | 9/2004 | Chern Lin et al. | |
| 2004/0210297 A1 | 10/2004 | Lin et al. | |
| 2005/0015097 A1 | 1/2005 | Mujwid et al. | |
| 2005/0065609 A1 | 3/2005 | Wardlaw | |
| 2005/0090852 A1 | 4/2005 | Layne et al. | |
| 2005/0119662 A1* | 6/2005 | Reiley et al. | 606/92 |
| 2005/0143688 A1* | 6/2005 | Lin et al. | 604/60 |
| 2005/0228391 A1 | 10/2005 | Levy et al. | |
| 2005/0228397 A1 | 10/2005 | Malandain et al. | |
| 2005/0267483 A1 | 12/2005 | Middleton | |
| 2006/0079905 A1 | 4/2006 | Beyar et al. | |
| 2006/0155296 A1 | 7/2006 | Richter | |
| 2006/0229625 A1 | 10/2006 | Truckai et al. | |
| 2006/0247648 A1 | 11/2006 | Serbousek | |
| 2006/0271057 A1* | 11/2006 | Shluzas et al. | 606/86 |
| 2007/0055281 A1* | 3/2007 | Osorio et al. | 606/92 |
| 2007/0142765 A1 | 6/2007 | Lin et al. | |
| 2007/0156242 A1 | 7/2007 | Lin et al. | |
| 2009/0254132 A1 | 10/2009 | Scribner et al. | |
| 2011/0288522 A1 | 11/2011 | Hollowell et al. | |
| 2011/0288528 A1 | 11/2011 | Lin et al. | |
| 2011/0288530 A1 | 11/2011 | Yuan et al. | |
| 2011/0295231 A1 | 12/2011 | Lin et al. | |

FOREIGN PATENT DOCUMENTS

| | | |
|---|---|---|
| EP | 1 588 674 | 10/2005 |
| EP | 1 588 732 | 10/2005 |
| EP | 1 882 459 | 1/2008 |
| WO | WO 02/26170 A2 | 4/2002 |
| WO | WO 03/057088 A1 | 7/2003 |
| WO | WO 2009/036466 | 3/2009 |

OTHER PUBLICATIONS

International Search Report for PCT/US2005/031356, mailed Apr. 7, 2006.
International Search Report and Written Opinion for PCT/US2006/026727, mailed Jan. 29, 2007.
Chinese Office Action for 200680043269.1, mailed Sep. 25, 2009.
Chinese Office Action for 200680029705.X, mailed Jul. 10, 2009.
Chinese Office Action for 200680029705.X, mailed Dec. 15, 2010.
Chinese Office Action for 200580037847.6, mailed Jan. 22, 2010.
Chinese Office Action for 200580037847.6, mailed Oct. 19, 2011.
Chinese Office Action for 200580037847.6, mailed May 30, 2012.
Chinese Office Action for 200680043269.1, mailed May 7, 2010.
European Search Report for EP Application No. 06840005.0, mailed Nov. 29, 2011.
European Office Action for EP 05794205.4, mailed Oct. 2, 2009.
Final Office Action for U.S. Appl. No. 11/674,085, mailed Jun. 24, 2010.
Office Action for U.S. Appl. No. 11/674,085, mailed Nov. 4, 2009.
Office Action for U.S. Appl. No. 11/674,085, mailed Apr. 3, 2009.
Office Action for U.S. Appl. No. 11/674,085, mailed Apr. 22, 2008.
Office Action for U.S. Appl. No. 11/674,085, mailed Jun. 11, 2007.
Office Action for U.S. Appl. No. 10/652,470, mailed Mar. 13, 2006.
Office Action for U.S. Appl. No. 11/674,087 mailed Dec. 2, 2010.
Office Action for U.S. Appl. No. 11/562,803, mailed Jan. 7, 2009.
Office Action for U.S. Appl. No. 11/562,803, mailed Mar. 8, 2011.
Office Action for U.S. Appl. No. 11/674,088, mailed Jun. 8, 2007.
Office Action for U.S. Appl. No. 11/674,088, mailed Nov. 28, 2007.
Office Action for U.S. Appl. No. 11/674,088, mailed Apr. 22, 2008.
Office Action for U.S. Appl. No. 11/674,088, mailed Oct. 24, 2008.
Office Action for U.S. Appl. No. 11/674,088, mailed Jul. 9, 2009.
Office Action for U.S. Appl. No. 11/674,088, mailed Jan. 22, 2010.
Final Office Action for U.S. Appl. No. 11/674,088, mailed Jun. 24, 2010.
Office Action for U.S. Appl. No. 11/674,088, mailed Nov. 12, 2010.
Office Action for U.S. Appl. No. 13/196,221, mailed Sep. 24, 2012.
Office Action for U.S. Appl. No. 11/574,562, mailed May 1, 2009.
Office Action for U.S. Appl. No. 12/829,500, mailed Nov. 10, 2010.
Office Action for U.S. Appl. No. 11/994,838, mailed May 24, 2011.
Final Office Action for U.S. Appl. No. 11/994,838, mailed Mar. 14, 2012.
Office Action for U.S. Appl. No. 13/195,490, mailed Jan. 3, 2013.
Office Action for U.S. Appl. No. 13/195,483, mailed Jan. 3, 2013.

* cited by examiner

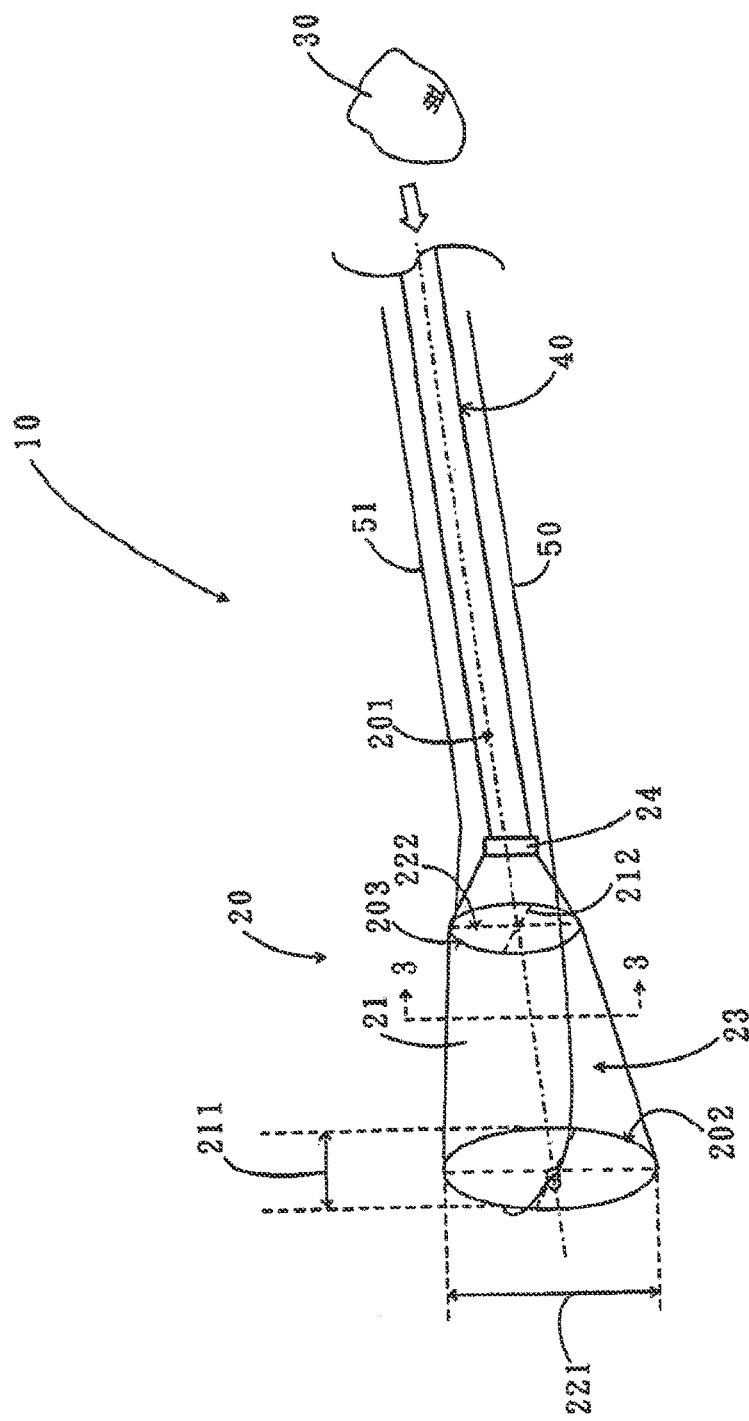

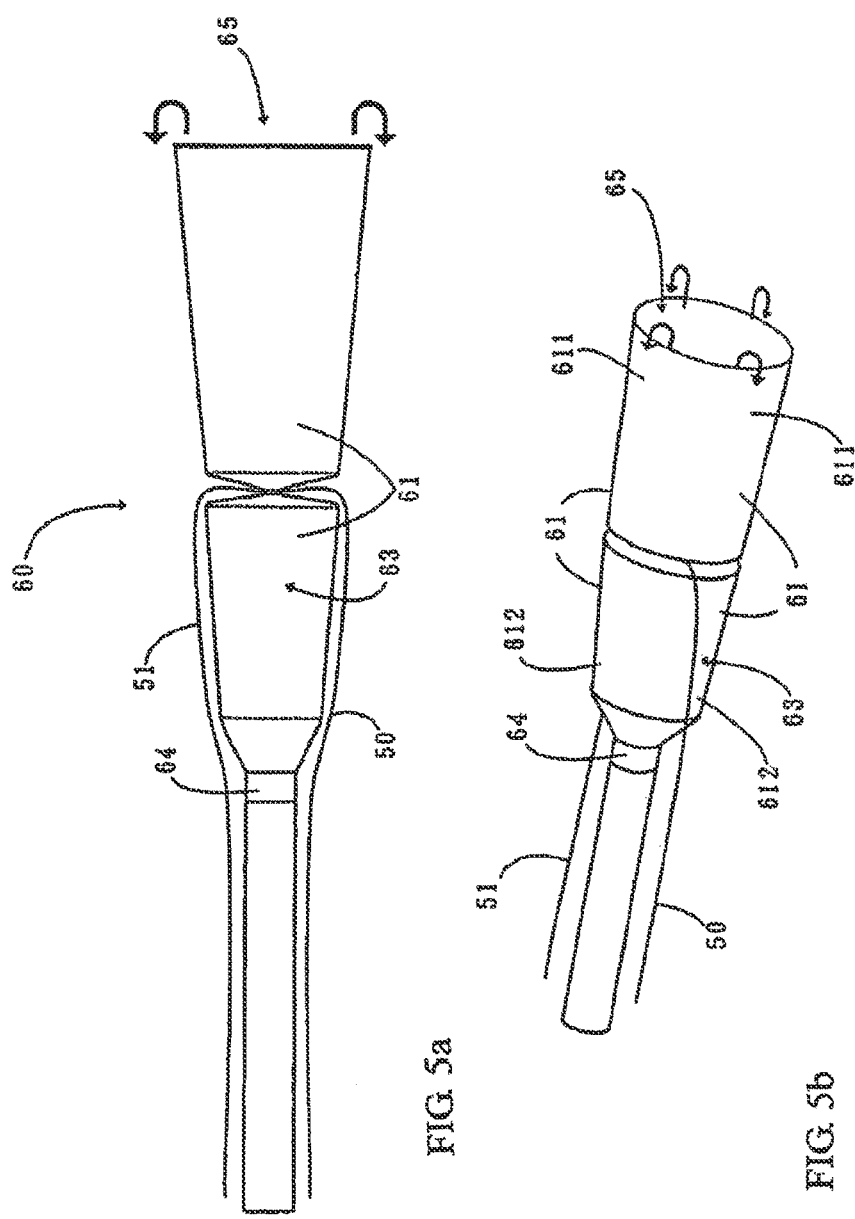

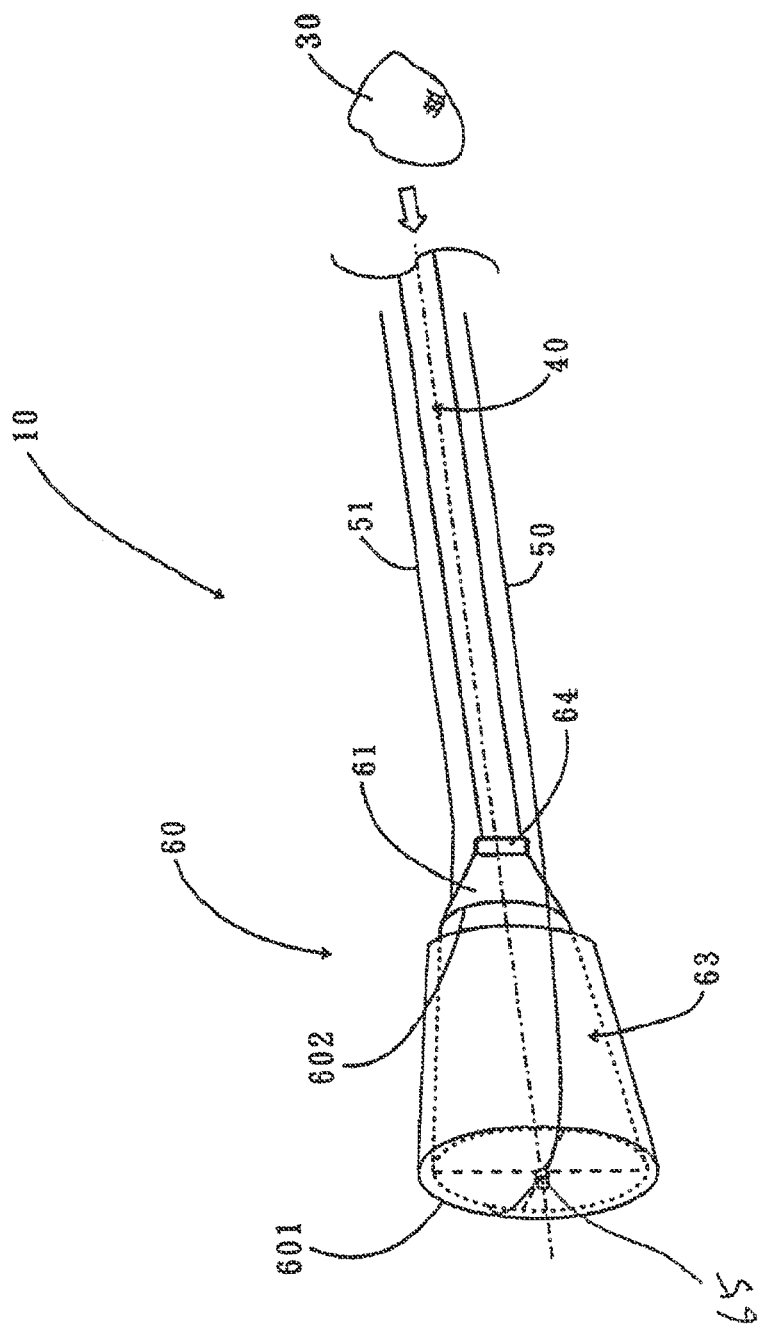

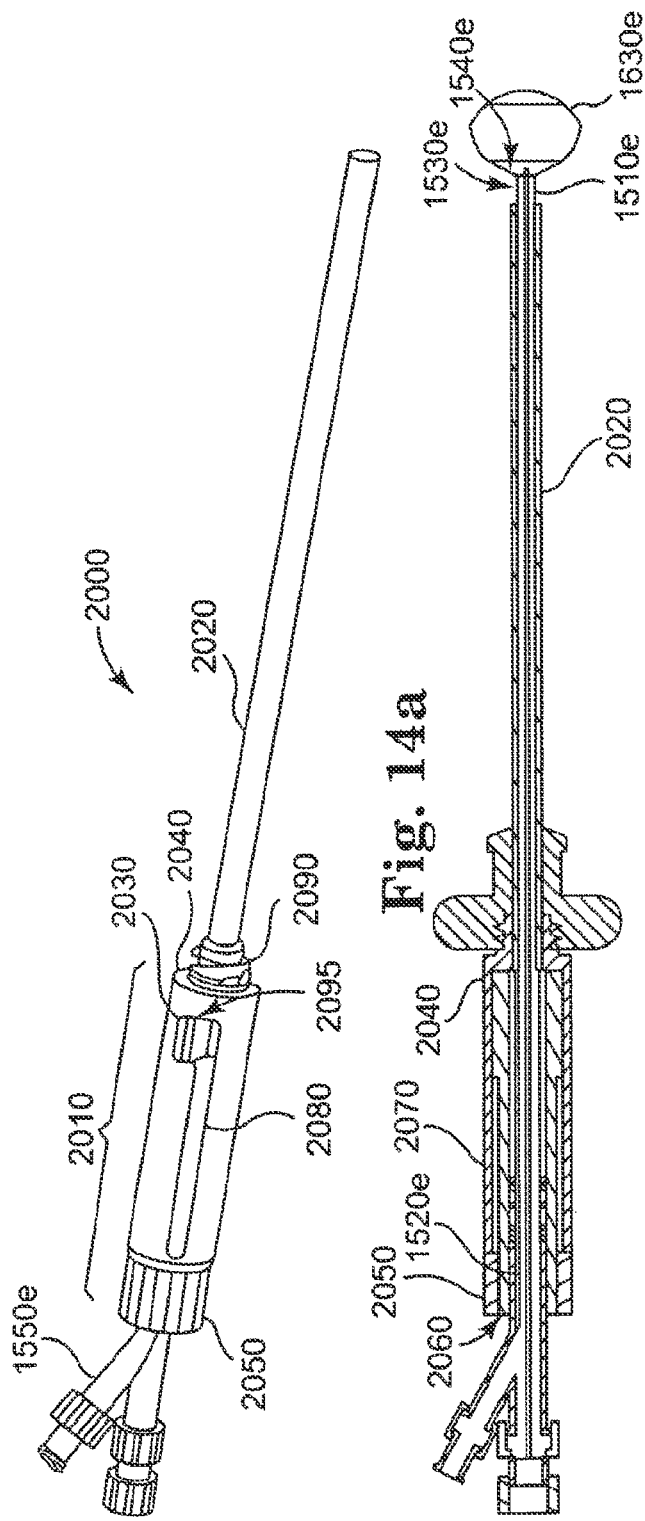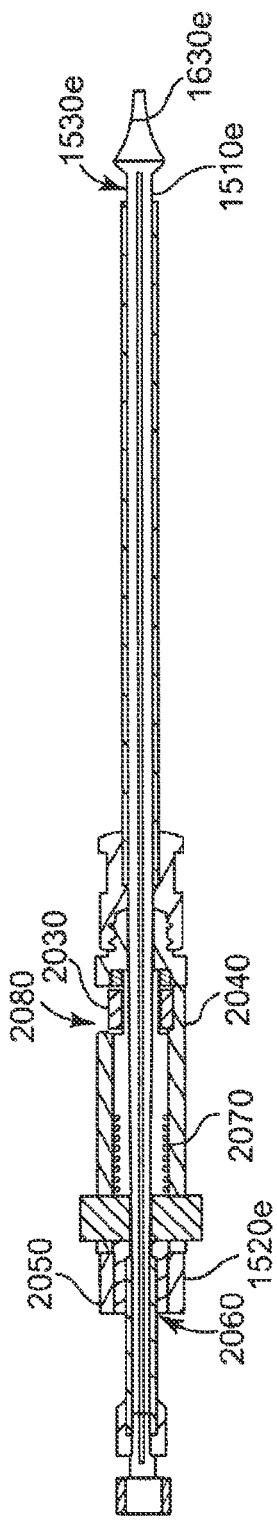
Fig. 14a
Fig. 14b
Fig. 14c

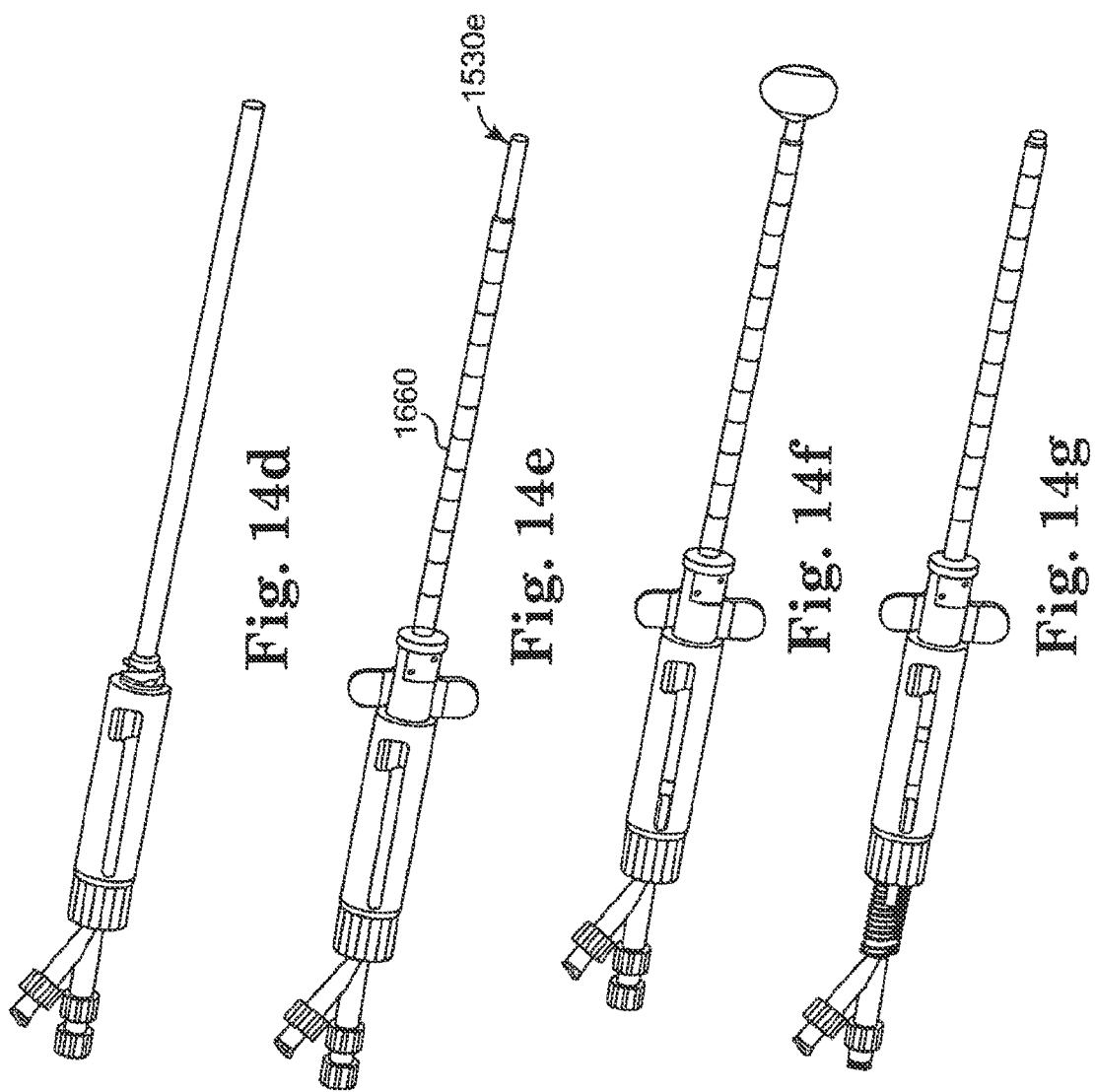

MATERIAL CONTROL DEVICE FOR INSERTING MATERIAL INTO A TARGETED ANATOMICAL REGION

This application claims priority to and the benefit under 35 U.S.C. §371 of PCT Application No. PCT/US2008/076463, filed Sep. 15, 2008, which claims priority to and the benefit of U.S. Provisional Application No. 60/993,751, filed Sep. 14, 2007, the disclosure of each of which is incorporated by reference herein in its entirety.

FIELD OF THE INVENTION

The present invention relates generally to instruments that can be used in the control and/or containment of medical materials, alone or in combinations with additional surgical instruments and/or procedures used in restorative operations of targeted anatomical regions, including, for example, within the intervertebral disc space and/or within or between one or more vertebral bodies of the human spine. More specifically, the disclosed surgical instruments can be used to insert a reinforcing, therapeutic or other type of medical material into a vertebral body such that the instrument can be separated from the material and partially and/or completely drawn out of the vertebral body, leaving some and/or all of the material within the vertebral body prior to, during and/or after removal of the instrument.

BACKGROUND AND SUMMARY OF THE INVENTION

The surgical treatment of vertebral body disorders can often include one or more of the following surgical techniques and/or methods, including, but not limited to, the hypodermic (or percutaneous) introduction of one or more materials, the balloon-assisted or mechanically assisted (minimally-invasive or non-open) introduction of one or more materials, the use of open and/or semi-open surgical access procedures, and/or the removable filling-device-assisted introduction of one or more materials. For example, U.S. Pat. Nos. 5,972,105; 6,066,154; and 6,248,110 disclose methods for treating bone tissue disorders, such as osteoporosis and/or vertebral compression fractures. The methods disclosed in these patents, the disclosures of which are incorporated herein by reference, involve the use of various surgical instruments, such as a surgical balloon and/or other enlargeable/expandable structures (for example, balloons made by Kyphon Corp. of Sunnyvale, Calif. U.S.A. or mechanically expanding devices made by Medtronic Corp.) by which the hard and/or soft tissue can be displaced, expanded and/or compressed to facilitate the creation of a body cavity and/or the inserting of a medicine. While an effective procedure, one drawback of this balloon method is that the technique generally permits the medicine or other filling material (introduced after cavity creation and balloon removal) to spread and/or flow in an uncontrolled, minimally-controlled and/or insufficiently controlled fashion within and/or beyond the targeted tissue regions and/or its boundaries. Without sufficient containment and/or control, the medicine and/or other materials may be limited and/or reduced in their effectiveness, and there is the potential for the material(s) to cause unintended injury to the surrounding tissues as well as undesirable consequences to the patient (such as where liquid PMMA polymerizes and/or solidifies in blood vessels, other bodily tissues and/or adjacent to tissues such as nerves, or where the patient is particularly susceptible to the effects of a component, intermediate product and/or by-product of the filler/stabilizing material, such as the cardiac depressive effects of the monomer component of PMMA). Similar concerns exist with the hypodermic/percutaneous injection of one or more materials, otherwise commonly known as vertebroplasty, which similarly involves the unconstrained injection of medicine or other filling materials into the targeted anatomical region.

Moreover, the balloon-assisted and/or mechanically-assisted cavity-creation techniques (and virtually all currently-existing techniques where a cavity is created and then subsequently filled through a percutaneous, minimally-invasive and/or non-open approach) require that the cavity-creating device be removed from the cavity and/or surgical access path prior to introduction of the filler and/or reinforcement material, thus leaving the cavity "free-standing" or unsupported for a period of time prior to introduction of the filler and/or reinforcement material. During this time of little or no support, the cavity may partially or fully collapse, bony fragments may displace in an undesirable manner, the natural anatomy of the treated region or the surrounding soft tissues may induce the targeted anatomical region to move or "rebound" from the desired displaced state and/or bodily fluids or tissues can undesirably collect within the cavity, reducing and/or eliminating the therapeutic effects of the surgical procedure and/or the effectiveness of any medicine or therapeutic material subsequently introduced during the material introduction stage, or inhibiting or preventing the introduction of such materials altogether.

Moreover, the balloon-assisted and/or mechanically-assisted cavity-creation techniques require an extensive array of surgical tools, both for cavity creation as well as subsequent filling of the cavity. In addition, these techniques typically involve a series of tool exchanges, each of which involves some level of surgical risk as well as an increased risk of infection at the surgical site.

Another disadvantage inherent in these surgical techniques involves the use of a polymerizing substance such as polymethylmethacrylate bone cement (PMMA). Such materials as PMMA must be introduced into the targeted anatomical region in a specific desired consistency: inject it too soon, and the material is too thin or "runny" and likely to extravasate in an undesired and potentially lethal manner; inject too late, and the material may be too thick or hardened to extrude from the injector, or may be too thick to travel down the surgical cannula, or may be too thick to properly fill the cavity.

In order to address the various disadvantages inherent in the balloon method, the filler-insertion method was developed, which facilitated the implantation of the medicine and/or other materials within the targeted vertebral body in such a way that the medicine and/or other material was initially fully contained within a boundary or other filler material (such as a membrane or some other structure), such that both the medicine or other material and the surrounding boundary or filler material were permanently implanted within the vertebral body during the procedure. One example of this method is described in U.S. Pat. No. 7,226,481 to Kuslich, the disclosure of which is incorporated herein by reference. While this alternate method could in some limited manner alleviate and/or reduce the dangers associated with unintended flow of the medicine and/or other material, this method also carried inherent drawbacks, including (1) the requirement for the boundary or filler material to be permanently implanted within the treatment site, thereby requiring the material to be biocompatible and/or creating a significant danger of the body's rejection of the boundary or filler material itself, (2) prevention of the medicine and/or other material from flowing into and/or fully integrating and/or interdigitating into the surrounding anatomical tissues, such as the cancellous bone of a vertebral body, thereby significantly reducing the strength and durability of the surgical repair, as well as providing a boundary layer especially prone to the development of tissue necrosis and/or infection, and/or (3) prevention or inhibition of the passage of medical or other therapeutic materials from the implanted medicine into the surrounding tissues and/or remainder of the patient's body, if such actions were desired.

Moreover, none of the aforesaid treatments repeatedly and consistently focus on the objective of reducing and/or repairing depressed and/or fractured vertebral bodies, with the ultimate goal of retrieving the original spinal curvature. Instead, even successful performance of these procedures does not guarantee displacement and/or reduction of fractured surfaces, and all of the previously-mentioned techniques allow the front or anterior portion of the vertebra, which is prone to vertebral compression fractures and/or further collapse, to remain insufficiently supported, and thus the patient is apt to experience and/or regain issues with vertebral collapse subsequent to the implantation surgery.

The invention disclosed herein includes the recognition of a need in the art for surgical tools and techniques that permit the controlled, directed and/or contained introduction of medical materials into a targeted anatomical region, including those materials utilized in restorative and/or augmentation operations of vertebral body disorders and those utilized in combination with surgical devices and/or procedures useful for creating, enlarging, altering and/or filling cavities or other openings within targeted anatomical regions. More specifically, the disclosed surgical instruments and methods are utilized to control and/or induce the insertion of a medical material into a vertebral body in a controlled and/or directed manner such that the surgical instrument can be separated from the medical material and drawn out of the vertebral body, leaving some and/or all of the medical material within the targeted anatomical region, thereby allowing the material to remain and/or solidify in the vertebral body, or achieve some other therapeutic purpose, if desired. In addition, various embodiments of the disclosed surgical instruments and methods facilitate the modification and/or controlled/directed fracture/weakening of healthy bone and/or healed bone tissues to further facilitate reduction of vertebral body factures and the ultimate reinforcement of the re-stabilized bony tissues. In addition, the disclosed surgical instruments and methods can be utilized to simultaneously compress and/or manipulate surrounding tissues during introduction of the medical materials, and then immediately bear loads and/or support the surrounding anatomy, thereby eliminating the opportunity for such tissues to move or "rebound" when unsupported during the steps of removing a surgical support tool prior to insertion of one or more structural medical support materials.

In various alternative embodiments, the devices described herein, as well as those constructed in accordance with various teachings of the present invention, could be utilized for a myriad of different medical or therapeutic purposes, including the direction and of control of materials and/or other therapeutic substances introduced to treat degenerative disc disease (i.e., nucleus repair/replacement and/or artificial disc repair/replacement in the intervertebral space) or treatment of venous or arterial aneurisms (i.e., filling control device for filling, but not occluding, a targeted aneurism). Similarly, the various teachings of the present invention may be useful for the treatment of blocked or partially occluded veins and arteries (i.e., angioplasty or rotablation, etc.), pulmonary applications such as reopening collapsed bronchial tubes and/or treatment of nasal sinus passages. If necessary, the design of the present invention can be altered (if desired) to accommodate passage and use of the tools through a variety of surgical access tools, such as surgical cannulae, laparoscopic access ports, cardiac catheters, bronchoscopes, etc., as necessary.

The disclosed devices could be utilized in correcting deformities in upper and lower extremities (i.e., replacing or repairing bone loss due to diabetes, osteoporosis, etc.), to occlude peripheral vessels to prevent blood flow to specific anatomical areas (i.e., treating varicose veins) or to redirect blood flow to critical areas (i.e., isolate larger extremities to redirect blood flow to critical organs and/or the brain, etc.). The disclosed devices could also be used to control the targeted delivery of medications to a desired location and/or be used to create a slow-release packet of medication.

In addition, the present invention may have particular utility where the bone or other targeted anatomical structure(s) may be especially prone to allowing flowable materials to pass outside of the targeted anatomy, with undesirable consequences. Such instances could include where surgical tools have been used to create additional fractures in a vertebral body or other bone (such as in the cortical rim surrounding a vertebral body), where the bone has suffered from a traumatic and/or "high-velocity" fracture, and/or where the vascularization of the targeted anatomy is especially susceptible to passage of the flowable material.

The disclosed devices may also have particular utility where it is desirous to create an anchoring region or location for devices (including orthopedic joint replacement implants) somewhere in the targeted anatomical region. For example, where pedicle screws have failed and/or "pulled out" of a patient, it may be desirous to reattach new screws in the same location(s). In such an instance, it would be possible to utilize the tools and techniques of the present invention to create a cavity within the targeted anatomical region, fill the cavity with a settable material, and subsequently introduce the device (or an anchoring or other component section of the device) into the settable material, thereby creating a solid anchoring region where the natural anatomy would not be capable or suitable for such load.

The disclosed surgical procedures can be performed on an outpatient or inpatient basis by a medical professional properly trained and qualified to perform the disclosed procedures. Desirably, the patient will be placed under general or local anesthetic for the duration of the surgical procedures.

One embodiment of the disclosed surgical device includes an extractable device for inserting a medicinal filling into a vertebral body, said device comprising:

a filling member comprising a flexible wall and provided with a holding portion, an injection port at one end of the holding portion, and an opening at another end of the holding portion;

one or more threads or opening members, each having one end for fastening releasably said opening of said holding portion in such a manner that said opening is leakproof and/or leak resistant; and a pasty medicine or other type of material(s) to be injected into said holding portion via said injection port of said filling member in the wake of a process for inserting said filling member into the vertebral body whereby said pasty medicine solidifies in said holding portion of said filling member;

said opening of said holding portion being unfastened at the time when a second end of said one or more threads (or other opening and/or releasing mechanisms) is pulled by an external force, thereby enabling said filling member to be extracted from the vertebral body so as to leave only said medicine in the vertebral body, wherein said holding portion of said filling member is inflatable and is substantially tubular (or other desired shape or configuration) after being inflated, wherein cross sections perpendicular to a longitudinal axis of the holding portion are substantially elliptical and have increasing areas thereof along a direction from the injection port to the opening of the holding portion.

Preferably, said flexible wall is provided with a plurality of through holes and is permeable. Said flexible and permeable wall is of a one-layered or multi-layered construction.

Preferably, said pasty medicine is a mixture of a liquid and a medicinal powdered substance or medicinal granular substance.

Preferably, the device of the present invention further comprises an injection tool for injecting said pasty medicine into said holding portion via said injection port.

Preferably, said injection tool comprises a guide tube and a syringe, wherein one end of said guide tube is connected to said injection port of said filling member and another end of said guide tube is connected to said syringe in which said pasty medicine is held, so that said pasty medicine is able to be injected into said holding portion of said filling member by said syringe via said injection port and said guide tube.

Preferably, the device of the present invention further comprises a working tube for inserting into said vertebral body, so that said filling member together with said guide tube can be inserted into said working tube and said filling member can be disposed and/or placed in said vertebral body.

In one embodiment, said flexible wall is a folded double-layer tubular wall having an inner layer end and a folded double-layer end, wherein said injection port of said holding portion is provided at said inner layer end, and said opening of said holding portion is provided at said folded double-layer end, wherein said medicine is released from said filling member by pulling a free end of an outer layer of the double-layer tubular wall to retreat the folded double-layer end, after said opening of said holding portion being unfastened. More preferably, said one or more thread is between an inner layer and said outer layer of said double-layer tubular wall. In various alternative embodiments, the flexible wall may be of single-layer construction, with any number (including only one) of a locking or sealing mechanism which desirably secures (and ultimately unfastens) the prior-created opening in the flexible wall.

In one alternative embodiment, said inner layer and said outer layer of said double-layer tubular wall are provided with a plurality of through holes and are permeable.

The present invention also discloses a method for implanting a solidified medicine or other material(s) into a vertebral body comprising:
  inserting a filling member in a hole of a vertebral body, said filling member comprising a flexible and permeable wall and provided with a holding portion, an injection port at one end of the holding portion, and an opening at another end of the holding portion, wherein one or more threads is provided and each having one end fastening releasably said opening of said holding portion in such a manner that said opening is leakproof and/or leak resistant, wherein said holding portion of said filling member is inflatable and is substantially tubular after being inflated, wherein cross sections perpendicular to a longitudinal axis of the holding portion are substantially elliptical and have increasing areas thereof along a direction from the injection port to the opening of the holding portion;
  injecting a pasty medicine into said holding portion via said injection port of said filling member, so that said holding portion is inflated 10 and said pasty medicine solidifies in said holding portion of said filling member; and
  unfastening said opening of said holding portion by pulling another end of said threads, thereby enabling said filling member to be extracted from the vertebral body so as to leave only said solidified medicine in the vertebral body, wherein said solidified pasty medicine has a shape similar to that of the inflated holding portion, and a cross section having a greater area of said solidified medicine is closer to a cortical rim opposite to a pedicle of said vertebral body in comparison with a cross section having a smaller area of said solidified medicine.

Preferably, the method of the present invention further comprises fastening detachably an injection tool with said filling member, so that said pasty medicine is injected into said holding portion via said injection tool. More preferably, said injection tool comprises a guide tube and a syringe, wherein one end of said guide tube is connected to said injection port of said filling member and another end of said guide tube is connected to said syringe in which said pasty medicine is held, wherein said pasty medicine is injected into said holding portion of said filling member by said syringe via said injection port and said guide tube.

Preferably, the method of the present invention further comprises inserting a working tube in said hole of said vertebral body, and inserting said filling member together with said guide tube into said working tube, so that said filling member is disposed in said vertebral body.

The flexible wall of the filling member of the present invention is preferably comprised of a biocompatible or biosynthetic material, such as rubber, elastic plastic, titanium, goat intestine, and the like, although, because the disclosure of the present invention can be utilized with equally utility with a material that need not necessarily remain permanently within the treated anatomy, the filling member may be comprised of virtually any material, even those materials that are not biocompatible (either over short or longer terms) to the patient. In various alternative embodiments, the flexible wall may comprise a biodegradable, bioabsorbable and/or bio-remodelable material with, if desired, one or more releasable couplings position at various point(s) located between some or all of the filling member and the holding portion. In another alternative embodiment, the filling member could comprise a flexible material incorporating an expandable metal mesh (i.e., expandable cages or stents of various configurations) embedded within the flexible material.

In various embodiments, the flexible wall can be provided with a plurality of pores in some and/or all of the wall material, and is therefore, in these various embodiments, permeable to a lesser or greater extent, depending upon the viscosity and/or flow characteristics of the medicine or material contained therein. Of course, if desired the flexible wall may comprise an impermeable or semipermeable material (i.e., a material allowing osmotic or other through-wall transfer or materials or components of materials). If desired, the flexible wall can be formed into a regular or irregular shape, including an object in the form of a sack, bag, ball, cylinder or rectangular column integrally or by joining separate pieces. In various alternative embodiments, the filling member may have a plurality of closable openings, whereby one or more control mechanisms may selectively open (and or reclose, if desired) one or more of these closable openings in a physician-directed fashion, as need arises.

The filling member and/or implanted medical materials of the present invention may contain a ray imaging and/or radiopaque material, such as a metal wire or particulates, or other non-direct visualization material and/or method, by which the precise position of the filling member can be easily located by a non-direct visualization imaging system, such as an X-ray machine. In various alternative embodiments, the filling member itself may comprise, incorporate, contain or be coated with other materials that can be detected by various other non-invasive and/or minimally invasive visualization systems, include fluoroscopes, x-ray detection equipment, CT-scanning machinery, MRI units, magnetometers and/or ultrasound detection equipment. Alternative embodiments could be utilized in conjunction with minimally or non-invasive (i.e., non-direct) surgical visualization systems introduced through the same or alternative access paths to the targeted anatomical treatment location.

The flexible wall of the filling member of the present invention may be of a one-layered or multilayered construction, depending on the particle size and/or the viscosity of the medicine. If the particle size of the medicine is relatively large, or the anticipated resistance of the environment to the introduction of the medicine is significant, the flexible wall is can comprise a two or more-layered construction. If the viscosity of the medicine is relatively high, the flexible wall is also preferably of a two-layered construction. On the other hand, the flexible wall could also be of a three-layered or four-layered (or more) construction under the circumstances that the particle size of the medicine is relatively small and/or the viscosity of the medicine is relatively lower. In alternative embodiments, the filler member may comprise a plurality of layers, some of which are particularly well-suited to be detachable or "left-behind" subsequent to introduction of the medicine and removal of the remainder of the filler member located within the detachable layer(s). Such detachable layer (s) could comprise, but is not limited to, differing materials from the remaining removable layer(s) of the filing material, such as a wire mesh (i.e., expandable cages or stents of various configurations) optionally embedded within a flexible layer of deformable material, a durable jacketing layer (i.e., a thin Kevlar, or other layer), a layer of therapeutic material (i.e., medications, fluid coagulation-inducing materials) and/or an insulating layer.

The features and the advantages of the present invention will be more readily understood upon a thoughtful deliberation of the following detailed description of the preferred embodiments of the present invention with reference to the accompanying drawings.

BRIEF DESCRIPTION OF THE DRAWINGS

FIG. 1 shows a schematic view of an extractable filler of the present invention.

FIGS. 5a and 5b are schematic views illustrating a process in which a double-layer wall of the holding portion of the filling member of the present invention is formed.

FIG. 5c is a schematic view of the extractable filler shown in FIGS. 5a and 5b after the double layer wall of the holding portion of the filling member is formed.

FIG. 9b is a longitudinal cross-sectional view of the filling member of FIG. 9a.

FIG. 9e is a partial perspective view of the sheath advancement/withdrawal mechanism of FIG. 9a.

FIG. 12b is a longitudinal cross-sectional view of the compression fitting of FIG. 12a.

FIG. 13c is a partial perspective view of the telescoping sheath of FIG. 13a.

FIG. 14a is a view of another alternate embodiment of a filling member constructed in accordance with the teachings of the present invention.

FIG. 14b is a longitudinal cross-sectional side view of the filling member of FIG. 14a.

FIG. 14c is a cutaway top plan view of the filling member of FIG. 14a.

FIGS. 14d through 14g are perspective views of the filing member of FIG. 14a, when introduced, deployed, retracted and withdrawn from the targeted anatomy.

DETAILED DESCRIPTION OF THE PREFERRED EMBODIMENTS

Figure 2A:
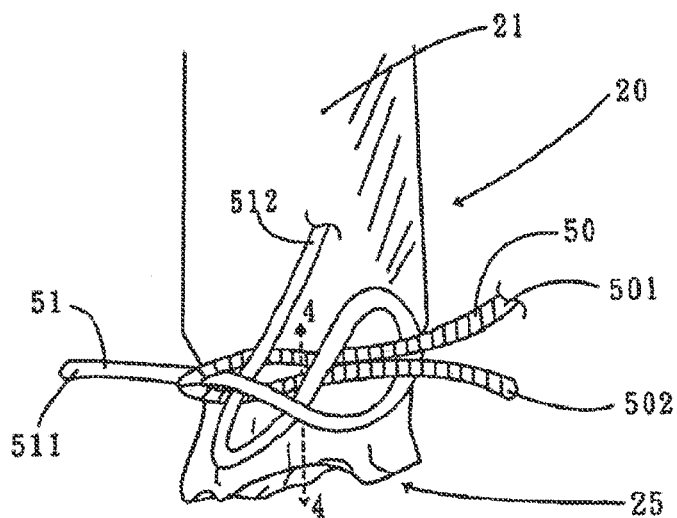
FIGS. 2a and 2b are schematic views illustrating one embodiment of a releasable closing mechanism or lashing of the opening of the holding portion of the filling member of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

The systems and methods embodying the invention can be adapted for use virtually in any interior body region, where the formation of a cavity or void within tissue is required for a therapeutic or diagnostic purpose and/or where manipulation and/or displacement of tissues and/or other materials is desired. The preferred embodiments show the invention in association with systems and methods used to treat bones. This is because the systems and methods which embody the invention are well suited for use in this environment. It should further be understood that the instruments described herein may be used in association with applications outside of the spinal field such as, for example, to treat other types of bony and/or soft (i.e., connective and/or other inter-joint tissue) structures. It should also be appreciated that the systems and methods which embody features of the invention can be used in other interior body regions, as well. Such regions could include, but are not limited to, within the intervertebral disc space, between adjacent vertebral bodies, and or within and/or adjacent to such bones as the radius, the humerus, the femur, the tibia or the calcaneus. Other non-bone body regions are also contemplated by the present invention. It should also be understood that the teachings of the present invention could be applied by those skilled in the art to a wide variety of mammals and/or other animals, with varying results.

While the present invention described introduction of the various surgical tools into the vertebral body via a pedicular access, it should be understood that access to the vertebral body may also be accomplished by alternative anatomic placement of the instruments. Alternative access routes may include extrapedicular instrument placement, as in the thoracic spine, or posterolateral placement of the instruments avoiding placement within the pedicles of the vertebral body. As previously noted, access may also be accomplished laterally, or via an anterior approach. These routes will provide access for formation of one or more passages within the cancellous bone.

As shown in FIG. 1, one embodiment of an extractable filler 10 constructed in accordance with the teachings of the present invention comprises a filling member 20, a pasty medicine 30, a guide tube 40, and one or more threads 50 and 51. The filling member 20 is formed of a flexible wall 21 and is provided with a holding portion 23 and an injection port 24. If desired, the flexible wall 21 may be made of rubber or a flexible plastic or metallic or bio-prosthetic (i.e., allographic, autographic and/or xenographic biologic) material, and may (if desired) incorporate pores, openings or other types of perforated holes. The pasty medicine 30 (or other material(s) as is described later) is injected into the holding portion 23 via the guide tube 40 and the injection port 24. The dotted line 3-3 shows a direction in which a section of the filling member 20 is taken. In the disclosed embodiment, the holding portion 23 has a shape similar to a cone with a longitudinal axis 201, wherein two cross sections 202 and 203 perpendicular to the longitudinal axis 201 are elliptical. The cross section 202 has a short diameter 21 1 and a long diameter 221, and the cross section 203 has a short diameter 212 and a long diameter 222, wherein the short diameter 21 1 and the long diameter 221 are longer than the short diameter 212 and the long diameter 222, respectively. When the filling member 20 is inserted in a collapsed vertical body, the cross section 202 is desirably at a position closer to a cortical rim opposite to a pedicle of said vertebral body and the cross section 203 is at a position near to the cortical rim close to the pedicle of said vertebral body. Preferably, the long diameters 221 and 222 are in the same direction of the vertebral column.

The filling member may be comprised of a flexible and/or stretchable material common in medical device applications, including, but not limited to, plastics, polyethylene, mylar, rubber, nylon, polyurethane, braided or knitted/woven materials, metals, ceramics and/or composite materials. Desirably, the shaft attached to the filling member will comprise a material that is more resistant to expansion than the material of the filling member, including, but not limited to, stainless steel, ceramics, composite material and/or rigid plastics. In an alternate embodiment, similar materials for the filling member and the shaft may be used, but in different thickness and/or amounts, thereby inducing the filling member to be more prone to expansion than the shaft material, or they be formed of the same type and quantity of materials, but with the shaft material constrained and/or limited from expansion by a surrounding material, such as a surgical cannula, through which it passes. The filling member may be bonded directly to the shaft by various means well known in the art, including, but not limited to, means such as welding, melting, sewing, gluing or the like. In alternative embodiments, the filling member may be secured inside or outside of the shaft, or a combination thereof.

Figure 2B:
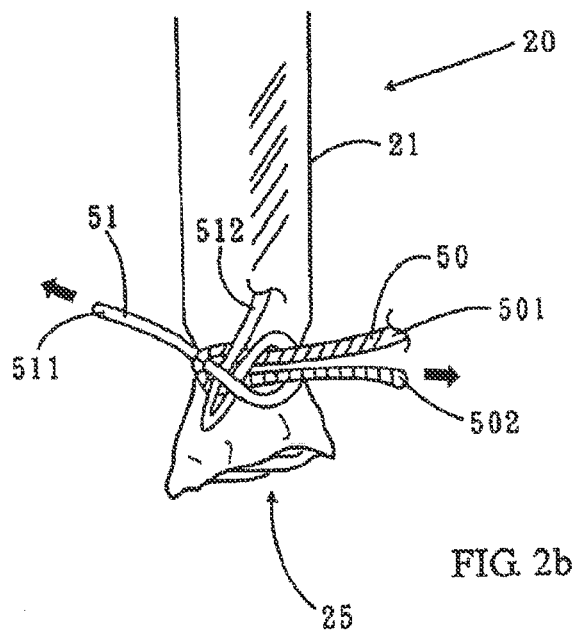

As shown in FIGS. 2a and 2b, the holding portion 23 of the filling member 20 is provided with an opening 25 opposite to the injection port 24 of the filling member 20 (although the opening could be located in other positions in the filling member, if desired). In this embodiment, the opening 25 is closed and/or lashed by two threads 50 and 51. The first thread 50 has a first end 501 and a second end 502, while the second thread 51 has a first end 511 and a second end 512. The two threads 50 and 51 are in fact fastened releasably to the flexible wall 21 near the opening 25. The threads may be secured in a variety of ways, including releasable knots and/or sewing-type closures.

The opening 25 of the holding portion 22 of the filling member 20 is securely tied up to desirably prevent and/or reduce the opportunity for the medicine 30 to leak out of the opening 25 by means of the two threads 50 and 51 which are releasably entangled in such a manner that the first end 51 of the second thread 51 is wound around the first thread 50.

Upon completion of the winding process, the flexible wall 21 surrounding the opening 25 is located in a position between the two threads 50 and 51, as indicated by a dotted line 4-4 in FIG. 2a. Thereafter, both ends 501 and 502 of the first thread 50, and the first end 511 of the second thread 51, are respectively pulled rightward and leftwards at the same time, as illustrated in FIG. 2b. As a result, the opening 25 of the filling member 20 is desirably leakproof and/or leak resistant. It should be understood that various objectives of the present invention may be realized by openings that are not leakproof and/or leak resistant per se, but rather are openings that reduce and/or constrict material flow to a meaningful degree. For example, a standard weaving or tailor's stitch could be utilized to secure the opening 25 to some meaningful degree.

Figure 3A:
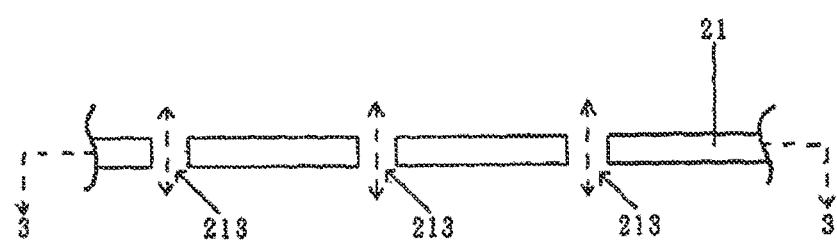
FIG. 3a shows a longitudinal sectional view of a one-layered wall of the filling member of the present invention.
Figure 3B:
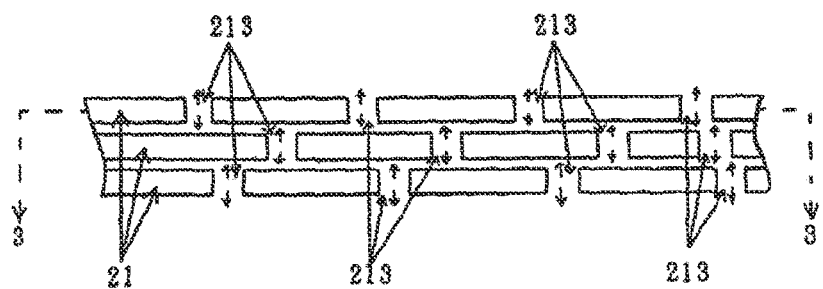
FIG. 3b shows a longitudinal sectional view of a multi-layered wall of the filling member of the present invention.

In various alternate embodiments, the flexible wall 21 of the filling member 20 can be constructed of a single-layer, as shown in FIG. 3a, or of a multi-layered construction, as shown in FIG. 3b. In the various embodiments, the use of fewer layers may be desired to reduce the thickness and/or overall profile of the flexible wall, especially in situations where the flexible wall 20 is utilized in a percutaneous or minimally-invasive surgical procedure. In some embodiments, the flexible wall 21 is provided with a plurality of pores 213 that are desirably permeable to fluids. If the flexible wall 21 is of a multi-layered construction, the flexible walls 21 can optionally be laminated in such a way that the pores 213 are not corresponding in location to slow down, limit and/or prevent the passage of fluids and/or small particulates.

If desired, the flexible wall could be constructed of multiple layers, such that one or more inner layers of material comprising the flexible wall incorporate one or more openable closures, while one or more outer layers of material comprising the flexible wall have no openable closures. In such an arrangement, the outer layers (without openable closures) could be intended to remain within the targeted anatomical region when the inner layers have been removed in the manner described herein.

Figure 4A:
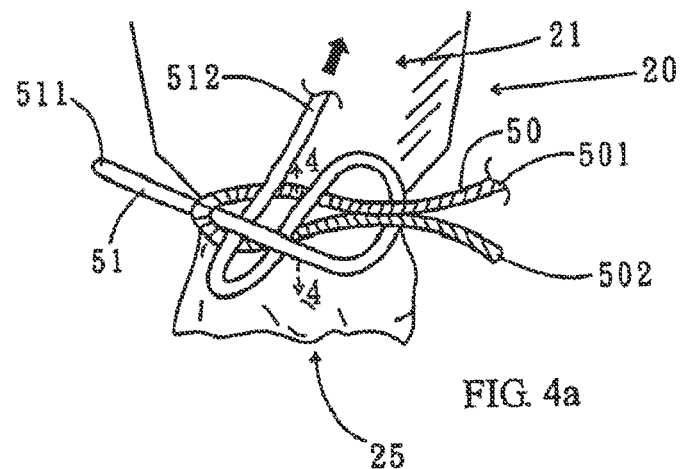
FIGS. 4a and 4b are schematic views illustrating the releasing or unlashing of the opening of the holding portion of the filling member of the present invention upon completion of the injection of the medicine into the holding portion of the filling member.

At a desired point in the surgery, the opening 25 of the filling member 20 may be untied or otherwise released when the second end 512 of the second thread 51 is pulled upward as indicated by an arrow in FIG. 4a. As a result, the two threads 50 and 51 become loosened. Thereafter, the first end 501 of the first thread 50 and the second end 512 of the second thread 51 are respectively pulled in a direction away from the opening 24 of the filling member 20, as illustrated in FIG. 5b. The opening 25 is thus partially or completely unfastened.

Figure 4B:
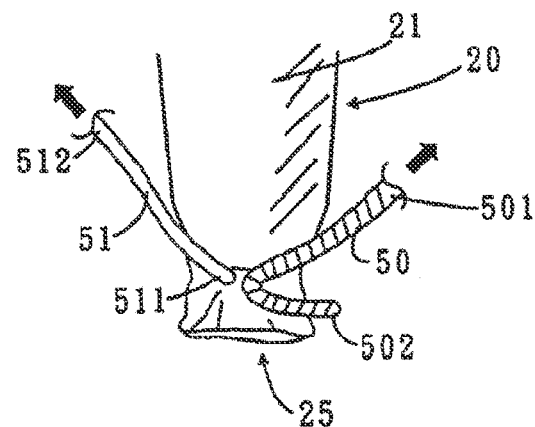

A further embodiment of the present invention is shown in FIGS. 5a, 5b and 5c, which is similar in some respects to the embodiment shown in FIGS. 1 to 4b. In this embodiment, a filling member 60 is depicted formed of a double-layer wall 61 and the first thread 51 and second thread 52 are located between an inner layer 612 and an outer layer 611 of the double-layer wall 61. As shown in FIGS. 5a and 5b, a flexible and permeable tubular wall having an injection port 64 at one end is tied at an intermediate point thereof by the threads 50 and 51 at the beginning. The lower portion 611 of the tubular wall (which will eventually become the outer layer) is then rolled up, so that the wall is inside out and covering up the threads 50 and 51 and the upper portion 612 of the tubular wall (the portion that will eventually become the inner layer). The rolled-up end of said double-layer wall 61 is provided with an opening 52 of the holding portion 63, which is secured or lashed by the two threads 50 and 51. The holding portion 63 as shown in FIG. 5c can have a conic shape, similar to the embodiment shown in FIG. 1, although a myriad of other shapes may be utilized, as necessary. The opening 65 can be unfastened by pulling the threads 50 and 51 the same way as shown in FIGS. 4a and 4b.

Figure 6A:
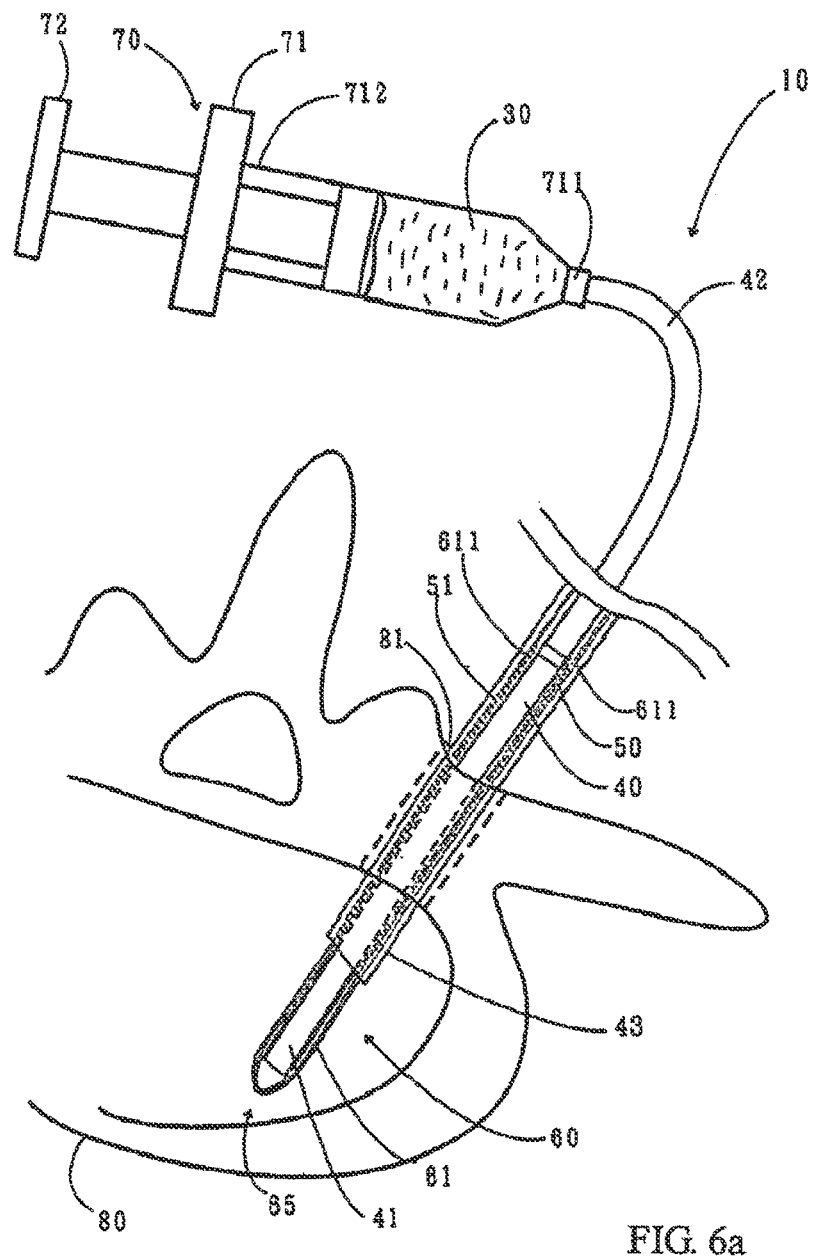
FIGS. 6a to 6c are sectional schematic views of the present invention at work.
Figure 6B:
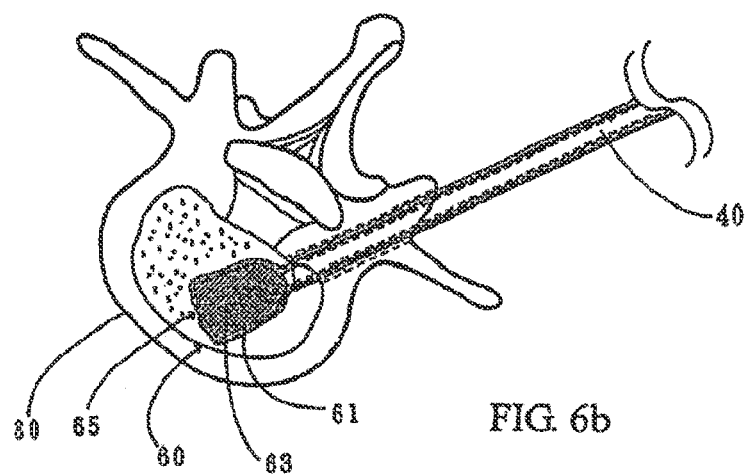
Figure 6C:
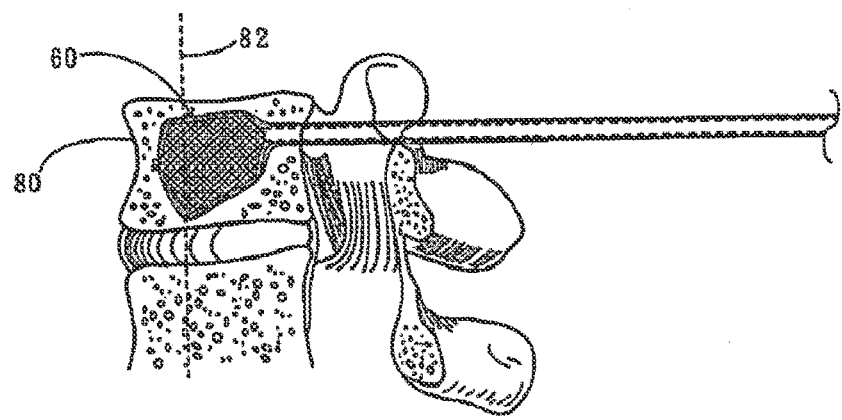

As shown in FIGS. 6a to 6c, the filling member 60 of the extractable filler 10 is inserted into a hole 81 formed in a vertebral body 80, wherein a working tube 43 is inserted into the hole 81 in advance to accommodate the guide tube 40, the threads 50 and 51 and the free end of the outer layer 611 of the double-layer wall 61 of the filling member 60. The pasty medicine 30 is then injected into the holding portion 63 of the filling member 60 by a syringe 70 in conjunction with the guide tube 40. The guide tube 40 has one end 41 in the holding portion 63, and another end 42 connected to one end 711 of a barrel 71 of the syringe 70. A plunger 72 is slidably inserted into another end 712 of the barrel 61 in which the pasty medicine 30 is contained. The filling member 60 is thus filled, expanded, enlarged and/or "inflated" by the medicine 30, as shown in FIGS. 6b and 6c, wherein the greater cross section 20 thereof is at a position closer to a cortical rim opposite to a pedicle of said vertebral body and the smaller cross section thereof is at a position near to the cortical rim close to the pedicle of said vertebral body. Preferably, the long diameters of the elliptical cross sections of the pasty medicine 30 are in the same direction of the vertebral column indicated by a dotted line 82 in FIG. 6c, whereby there may be enough room in the vertical body 80 for implanting two or more pasty medicines 30.

The pasty medicine 30 can take a myriad of forms, including a mixture of a liquid and one or more kinds of vertebral body drugs in the form of powder, granule, or colloid. The pasty medicine 30 is desirably capable of assuming a greater viscosity and, if desired, can completely solidify. If desired, the pasty medicine may comprise a load-bearing substance, such as polymethylmethacrylate, or bone cement.

Upon completion of the insertion of the pasty medicine 30 in the vertebral body 80, and any solidification or alteration in the viscosity of the material (if desired), the filling member 60 can be extracted from the hole 81 of the vertebral body 80, so as to leave only some or all of the medicine 30 within the vertebral body 80. By removing the filling member in this manner, the present invention desirably avoids and/or prevents the rejection of the filling member 60 by the human body. In the case of where the material is not completely solidified (or where the viscosity allows flowing and/or morphing of the material), extraction of the filling member prior to complete hardening of the material also allows for some meaningful degree of incorporation and/or interdigitation of the material with the surrounding anatomical structure(s), yet reduces the tendency for the material to flow that it would have had in its introduction state. In the embodiment disclosed in FIG. 4a, the extraction of the filling member 60 from the hole 81 of the vertebral body 80 involves a first step in which the second end 5 12 of the second thread 51 is pulled upward as indicated by an arrow in FIG. 4a. As a result, the two threads 50 and 51 become loosened. Thereafter, the first end 501 of the first thread 50 and the second end 512 of the second thread 51 are respectively pulled in a direction away from the opening 24 of the filling member 20, as illustrated in FIG. 4b. The opening 65 is thus unfastened completely.

It should be understood that the pasty medicine could comprise any single or combination of a variety of materials, including, but not limited to, medicines, artificial or natural body-replacement materials (i.e., allographic, autographic, xenographic and/or artificial tissues), therapeutic materials, reinforcing materials, load-bearing materials, bone mineral replacement materials, thixotropic materials, materials that harden or cure over time or in the presence of other materials, materials that do not significantly alter their viscosity and/or materials that soften or thin over time or in the presence of other materials. Alternatively, a granular or non-pasty material could be introduced into the filling member, and once the member was full, a vacuum could be drawn on the tool, desirably compressing or compacting the material into a form which could resist compressive or other loading. It should also be understood that the pasty medicine does not necessarily have to completely and/or significantly harden before opening and/or removal of the filling member. For example, it may be desirous for the filling member to only control and/or direct the flow of the medicine in some manner, either partially and/or completely through-out an introduction step. In an alternative embodiment, the filling member may control and/or direct the placement, position, direction and/or ultimate deposition of the medicine during an introduction/filling stage, and then be removed prior to the thickening, curing and/or hardening stage. In an alternative embodiment, the filling member may control and/or direct the placement, position, direction and/or ultimate deposition of the medicine during an introduction/filling stage, and then be removed partially through the thickening, curing and/or hardening stage. In another alternative embodiment, the filling member may control and/or direct the placement and/or position of the medicine during an introduction/filling stage, and continue such control and/or direction of placement, position, direction and/or ultimate deposition of the medicine completely through the thickening, curing and/or hardening of the material. At any planned stage during the surgical procedure, or if some unforeseen clinical need arises during the procedure, the filling member can desirably be removed during any stage of the surgical procedure, or can remain behind within the anatomical space (or other location within the patent's anatomy) for a limited time (either during additional surgical time or post-surgery) as well as permanently remain with the patient, as the clinician desires. If extended implantation is desired or necessitated, a cutting device or other instrument may be incorporated into the distal tip of the device to separate the filling member from the remainder of the surgical instrument prior to removal of the instrument from the vertebral body.

In alternate embodiments, the filling member can comprise a permeable, semi-permeable, or porous material, which desirably allows the transfer of medication or other material contained in the filling/stabilizing material (or introduced prior to, concurrent with and/or after the introduction of the filling/stabilizing material) into contact with the cancellous bone though the wall of the filling member, which desirably allows permeation, osmotic transfer and/or diffusion through the filling member. Similarly, the filling member may be perforated or allow various other forms of transport to allow some of the material (and/or a portion or component material thereof) to flow or pass through the wall of the filling member during the introduction/filling stage and/or afterwards. Alternatively, medication or other materials can be transported through the porous wall material by creating a pressure differential across the wall of the filling member.

As another embodiment, fluids, cells and/or other materials from the patients' body can pass and/or be drawn through the filling member for various purposes including, but not limited to, fluid/cellular analysis, bony ingrowth, bone marrow harvesting, and/or gene therapy (including gene replacement therapy). Various embodiments of the filling member could include single or multichamber devices (i.e., dual, triple, quadruple, or a greater number of chambers), with each chamber of the filling member being individually expandable using the filler/stabilizing material and/or inflation using an inflation material such as radiopaque fluid or saline. Use of such devices could allow the filling member to be placed in a desirable orientation using the inflation fluid-filled chambers, with one or more of the remaining chambers filled with a filling/stabilizing medium as disclosed in the present invention. Similarly, differing filling/stabilizing materials of different consistencies and/or components could be introduced into the various chambers of the filling member. In various embodiments where the one or more openings in the filling member can be selectively opened and/or closed, it may be desirous to introduce a medicine into the filling member, then release said opening to allow said medicine to enter a targeted anatomical region, then close the opening to allow introduction and retention of the same or a different medicine within the filling member (with these steps repeated as desired or necessary).

If desired, the closeable opening in the filling member could be opened at any point in the surgical procedure to allow the introduction of materials from the targeted anatomy, such as fluid or bodily tissue, to fill or permeate into any medicines or other materials contained within the filler member. For example, a medicine or therapeutic substance may be introduced into the targeted anatomy as previously described, and then the closeable opening could be opened and allow the ingress (or a vacuum drawn on the tool to draw such materials) of such fluids or other bodily tissues into the medicine or therapeutic substance. Such a technique could induce or allow blood and other materials (such as osteoclasts/osteoblasts or differentiated/undifferentiated stem cells) to permeate and/or lodge within the substance, thereby promoting bony ingrowth and/or consolidation of the material.

Figure 7A:
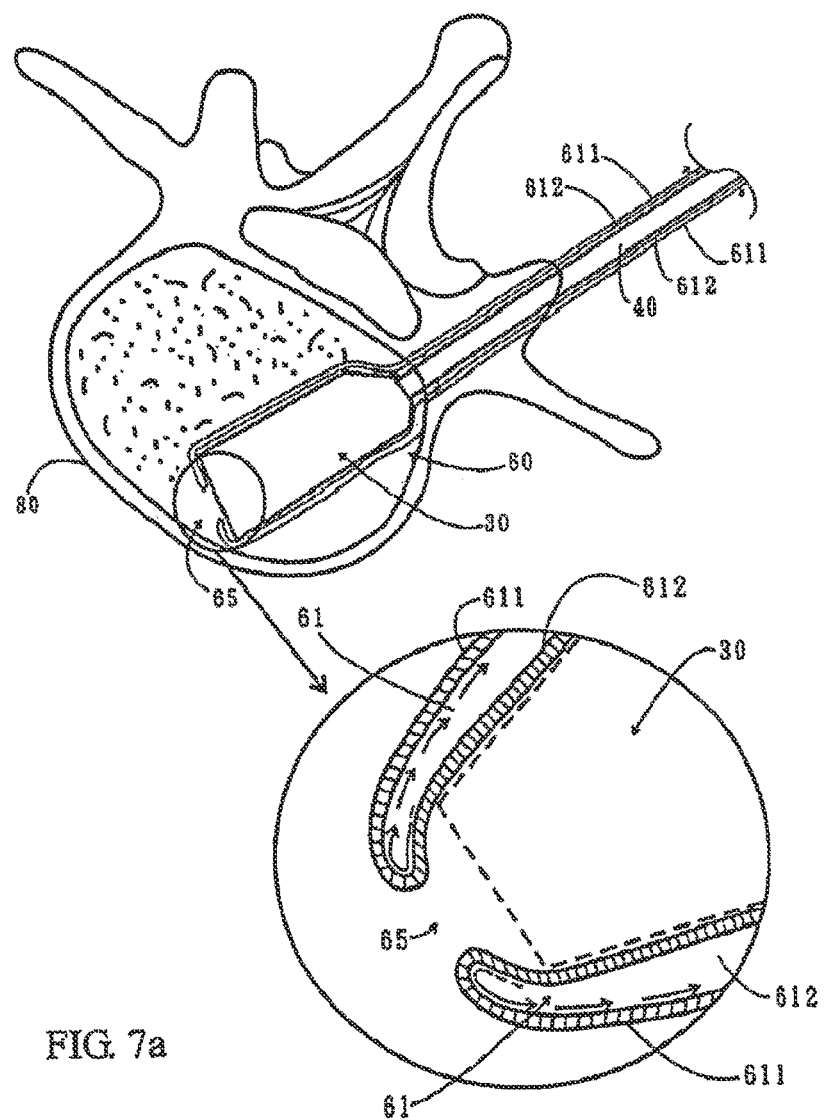
FIGS. 7a and 7b are sectional schematic views illustrating the process in which the filling member of the present invention is extracted from the vertebral body.
Figure 7B:
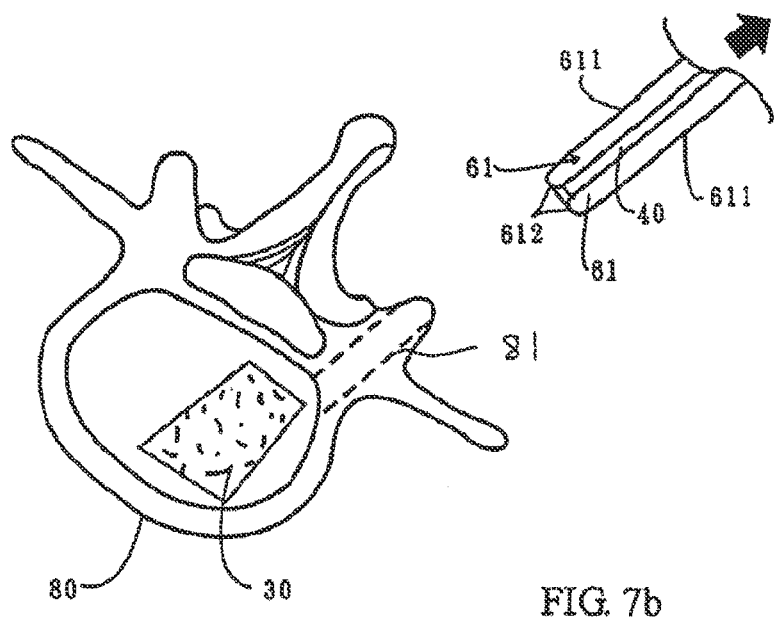

After the opening 65 is unfastened, the rolled-up double-layer end is retreated from the solidified medicine 30 by pulling a free end of the outer layer 611 of the double-layer wall 61, while one end of the inner layer 612 is connected to the guide tube 40 as an injection port of said holding portion of the said filling member 60, whereby said solidified medicine 30 is released from said filling member 60 and is disposed in the vertebral body 80, as shown in FIGS. 7a and 7b. The filling member and the guide tube 40 are pulled from the hole 81 of the vertebral body 80, so as to leave only said solidified or other medicine 30 in the vertebral body 80.

Figure 8A:
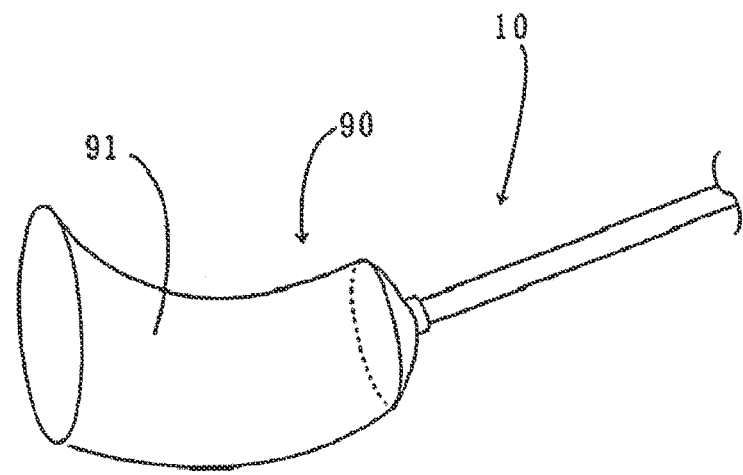
FIGS. 8a and 8b are schematic views illustrating that one embodiment of a holding portion of the filling member of the present invention has a curved profile.
Figure 8B:
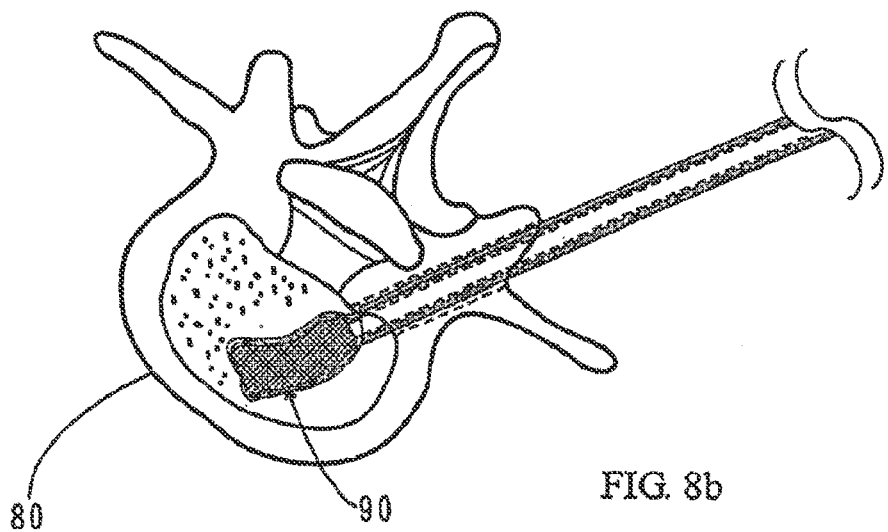
Figure 9A:
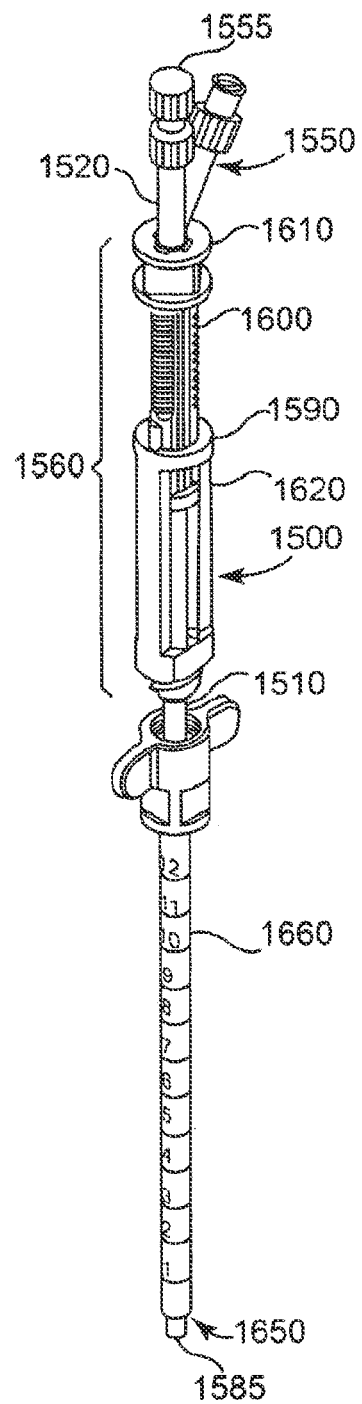
FIG. 9a is a perspective view of another alternate embodiment of a filling member constructed in accordance with the teachings of the present invention.
Figure 9B:
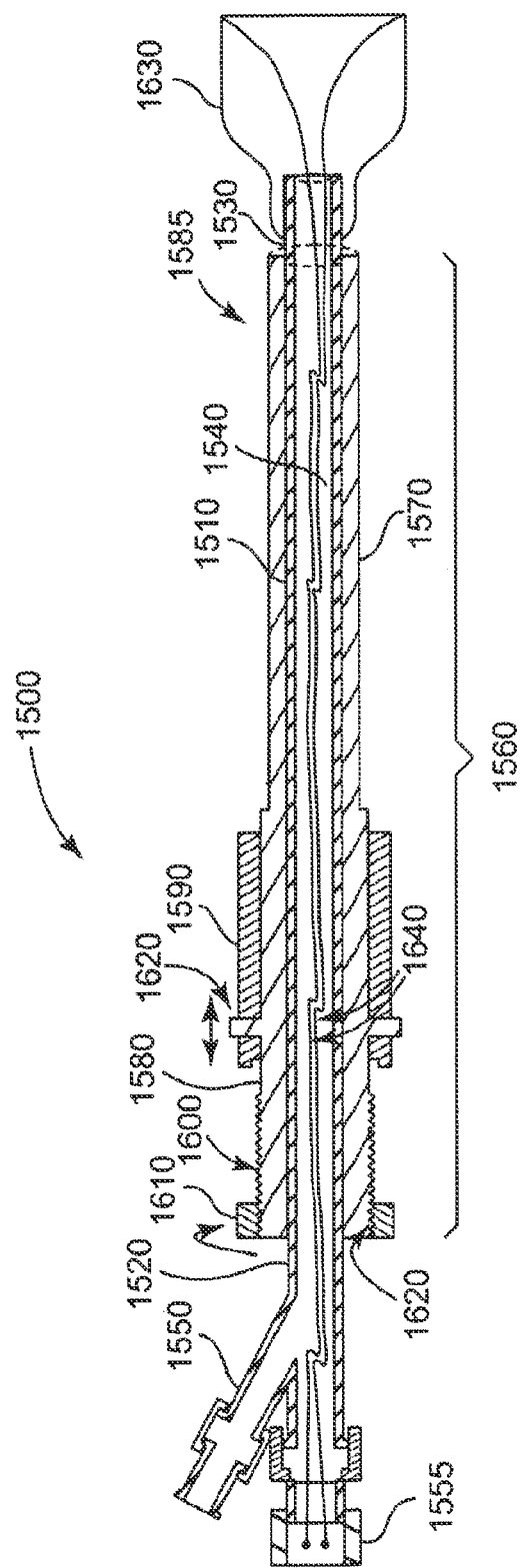
Figure 9C:
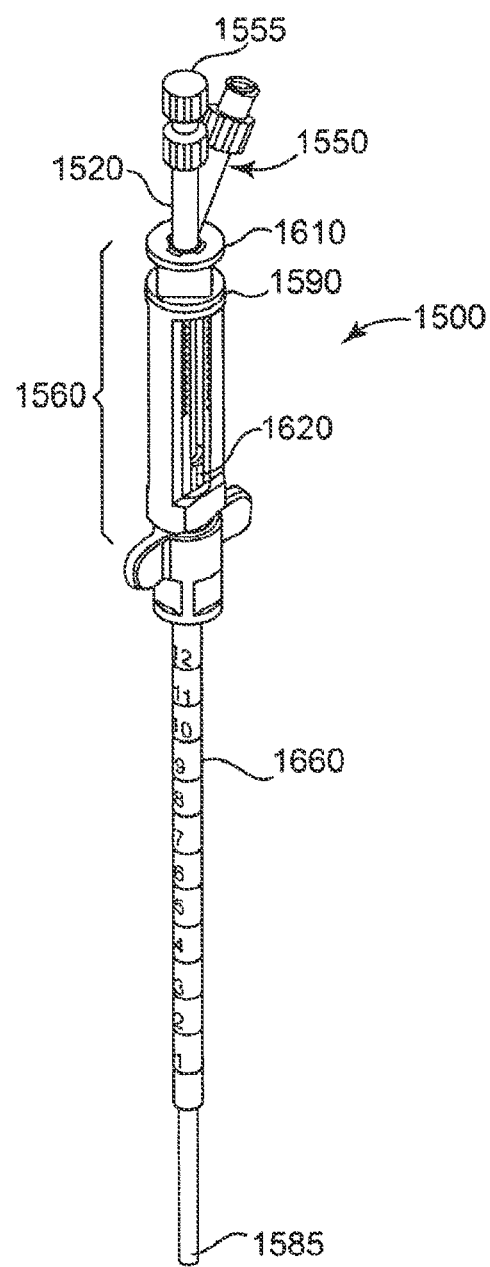
FIG. 9c is a perspective view of the filling member of FIG. 9a, as introduced to a targeted anatomical region.
Figure 9D:
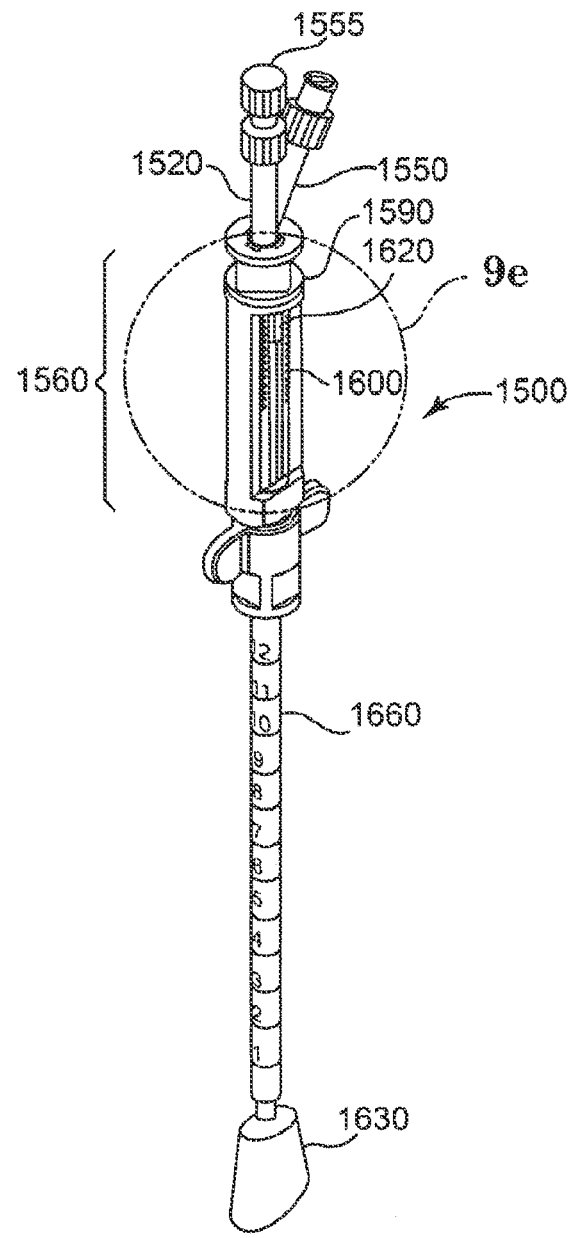
FIG. 9d is a perspective view of the filling member of FIG. 9a, depicting the sheath withdrawn from the filling member, and the filling member deployed and filled with a substance.
Figure 9E:
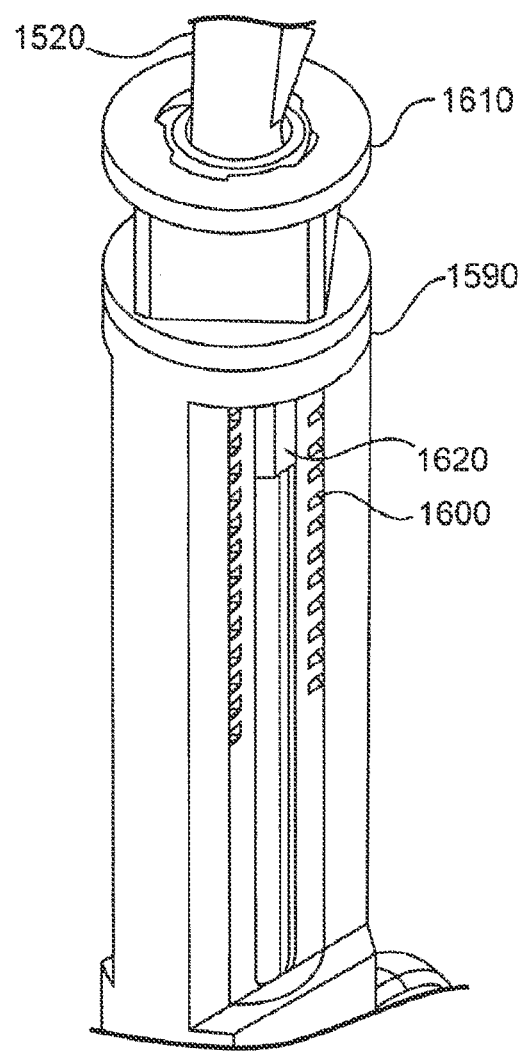
Figure 9F:
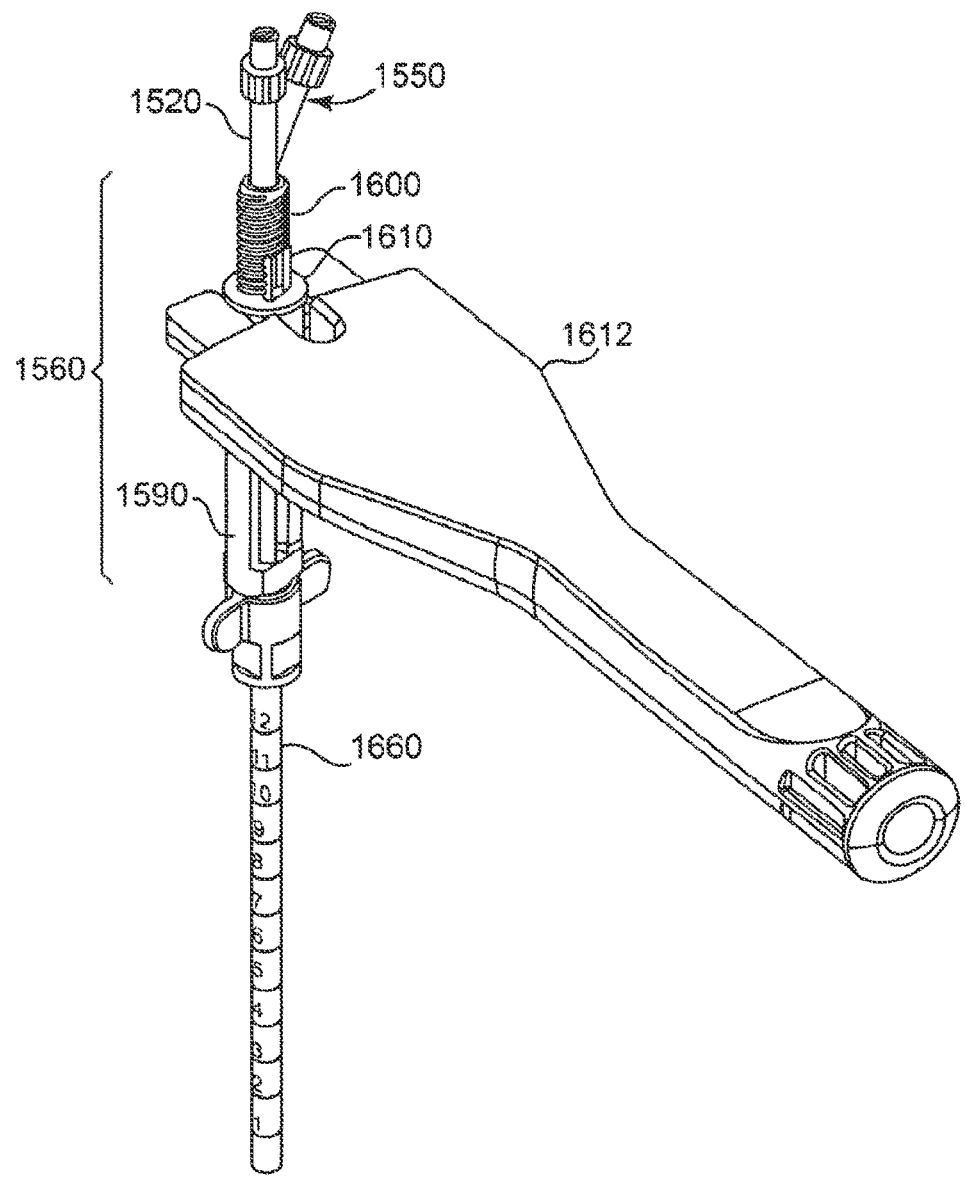
FIG. 9f is a perspective view of the filling member of FIG. 9a, with a rotatable arm connected to the withdrawal collar of the tool and depicting the filling member withdrawn into the sheath.

As shown in FIGS. 8a and 8b, the flexible wall 91 of the filling member 90 of the extractable filler 10 of the present invention may have a curved profile. Accordingly, the pasty medicine injected into the filling member 90 in the vertebral body can also desirably has a curved profile, if sufficiently hardened prior to removal of the filling member.

Cavity Creation and/or Modification

The devices and methods disclosed herein are particularly well-suited for use in creating, enlarging, altering and/or filling cavities or other openings within targeted anatomical regions, or can be utilized to varying degrees and/or utility in combination with surgical tools and/or techniques for creating cavities or modifying tissues within and/or around targeted anatomical regions, including within and around vertebral bodies of the spine. The devices and methods disclosed herein may similarly be utilized to displace, immobilize and/or manipulate cancellous and/or cortical bones of a targeted anatomical region, as well as regions between bones, such as between bones forming a joint space, including the intervertebral space (i.e., the space occupied by a healthy, diseased and/or damaged intervertebral spinal disc).

For example, in the treatment of bones having bone marrow therein, including bones containing cancellous bone and/or bone marrow, it may be desirous to introduce instruments of the system in a purposeful manner to penetrate hard and/or soft tissues and gain subcutaneous access to the interior of a bone and/or joint space. Inside bone, various instruments of the system and/or associated surgical tools can be deployed to form a cavity in cancellous bone and/or displace cancellous and/or cortical bone fragments to create a cavity or working space/region, into which a material can be placed for therapeutic purposes.

For example, one surgical instrument could comprise a conventional spinal needle assembly and a guide pin instrument. The spinal needle assembly could be utilized to establish an initial subcutaneous path leading to the targeted treatment site. If desired, a guide pin instrument could be deployed through this path, followed by progressively larger instruments.

Once the operative path is established, a cannula (or other access path instrument) can be introduced along the operative pathway. Desirably, the cannula will have an internal lumen sized to facilitate surgical access to the interior of the targeted anatomical area. If desired, an open surgical technique, or a less-invasive access technique utilizing expandable cannulae (such as the Atavi FlexPosure Retractor, commercially available from Endius, Incorporated of Plainville, Mass.), can be utilized with varying results. Once surgical access is established, a surgical tool can be introduced through the cannula to create, enlarge, reduce and/or modify the dimensions of a natural and/or artificial opening, recess and/or cavity within the targeted anatomical region.

In combination with the devices and methods of the present invention, various types and/or designs of additional surgical instruments could be utilized to create, enlarge, reduce and/or modify the dimensions of the opening, recess and/or cavity, depending upon the treatment area, the desired clinical outcomes, and/or the capabilities of the surgeon and/or surgical suite. Similarly, alternative methods of creating, enlarging, reducing and/or modifying the dimensions of the opening, recess and/or cavity could employed with varying degrees of utility, including chemical etching, dissolving, coagulating, dissipating and/or depositing of material.

Cutting Tools

For example, a useful additional surgical tool could comprise a mechanical or powered device to cut, sever, separate and/or dissolve tissues and/or tissue planes (including, but not limited to, hard tissues such as bone and bone marrow and/or softer tissues such as cartilage, connective tissues, muscles and/or fatty tissues). Such surgical devices could include, but certainly are not limited to, surgical scalpels, chisels, osteotomes, cutters, rongeurs, water knives and/or ultrasonic knives and the like. In cutting these tissues, such surgical tools could be utilized to create, modify, enlarge, reduce and/or alter the dimensions of the targeted anatomy before, during and/or after described introduction of the filling member and associated material(s). In addition, the use of such surgical tools could increase the likelihood of reducing a fractured region of bone (or other anatomical structure) by weakening healed and/or healthy bone and/or connective tissues along desired fracture lines, allowing the expansion of the filling member (and/or use of associated surgical devices such as tamps, etc) to displace some or all of the surrounding bony materials to a desired anatomical position. For example, commonly owned International Patent Application No. PCT/US06/26727, to Crosstrees Medical, Inc. and Scribner, et al, filed Jul. 7, 2006, the disclosure of which is incorporated herein by reference, discloses a method of weakening a fractured vertebral body along desired fracture planes, utilizing various surgical instruments such as cutting tools, to facilitate the use of a removable filling member to create a cavity and/or reduce the surrounding cortical bone portions.

It should also be understood that various embodiments of cutting tips for various cutting tools can be utilized to accomplish the cutting and/or bone separating features of the disclosed invention. In each case, the size and/or shape of the cutting tips could be optimized to fit the type of bone and/or specific environment for the bones in which they are to be utilized. In addition, these mechanical tools could be made of any biocompatible material (for example, but not limited to, stainless steel, titanium, titanium alloys, aluminum, aluminum alloys, chrome cobalt, pyrolytic carbon, polymers or ceramics) that has adequate shear and/or tensile strength to perform their bone manipulating functions. In addition, the material may be coated and/or encapsulated with a biocompatible material.

Cauterization Tools

As another example, a useful additional surgical tool could comprise a mechanical or powered device that desirably denatures, scars, burns and/or cauterize tissues, such as heated probes, lasers and/or cauterization instruments. In altering these tissues, such surgical tools could be utilized to create, modify, enlarge, reduce and/or alter the dimensions of the targeted anatomy before, during and/or after described introduction of the filling member and associated material(s). In addition, the use of such surgical tools could increase the likelihood of reducing a fractured region of bone (or other anatomical structure) by weakening healed and/or healthy bone and/or connective tissues along desired fracture lines, allowing the expansion of the filling member (and/or use of associated surgical devices such as tamps, etc) to displace some or all of the surrounding bony materials to a desired anatomical position.

Balloons and Compression Tools

As another example, a useful additional surgical tool could comprise a surgical device that compresses, crushes and/or displaces soft and/or hard tissues, including, but not limited to, expandable devices such as mechanical expanders, bone tamps, fluid expanded balloons, ultrasonic morselizers, brushes or rotating cutters, etc. In altering these tissues, such surgical tools could be utilized to create, modify, enlarge, reduce and/or alter the dimensions of the targeted anatomy before, during and/or after described introduction of the filling member and associated material(s). In addition, the use of such surgical tools could increase the likelihood of reducing a fractured region of bone (or other anatomical structure) by weakening healed and/or healthy bone and/or connective tissues along desired fracture lines, allowing the expansion of the filling member (and/or use of associated surgical devices such as tamps, etc) to displace some or all of the surrounding bony materials to a desired anatomical position.

If desired, the filling member of the present invention could be utilized with or without additional surgical tools to increase the size of a cavity within a targeted vertebral body (or other bone) by compressing surrounding cancellous bone and/or moving surrounding cortical bone. In such a case, introduction of a filling material into the filling member under sufficient force and/or pressure could cause an expansion of the filling member, thereby inducing an expansive force on surrounding tissues, and potentially creating a cavity within the bone and/or an internal reduction of any surrounding harder tissues, such as the cortical bone wall of a vertebral body suffering from a compression and/or high velocity fracture. Once the body tissues had obtained their desired position, the filling member could be removed at any point, including after the filling material was allowed to thicken (to prevent extravasation outside of the targeted anatomy) or harden and/or set (if desired), as previously described. Such a procedure could facilitate the internal reduction and fixation of a vertebral body compression fracture, for example, without fear of leakage of the filling material (such as a polymethylmethacrylate bone cement, its monomer component, or other artificial bone replacement materials) outside the vertebral body.

Desirably, compaction of the cancellous bone may have the effect of exerting an outward force on the inner surface of the cortical wall, making it possible to elevate or push broken and/or compressed bone back to or near its original pre-fracture condition or another desired condition. Alternatively, the filling member may bear directly against the inner surface of the cortical bone to reduce a compression fracture in the vertebral body. Once set to a hardened condition, the filling material provides internal structural support to the vertebral body, and more particularly provides structural support to the cortical bone of the vertebral body.

Chemical Processes

As another example, a useful additional method could incorporate the use of chemical processes to create enzymatic or chemical reactions which dissolve, coagulate, burn, etch or dissipate the surrounding hard and/or soft tissues. Similarly, such processes could be utilized to deposit or form additional materials within a targeted anatomical region. In altering these tissues, such methods could be utilized to create, modify, enlarge, reduce and/or alter the dimensions of the targeted anatomy before, during and/or after described introduction of the filling member and associated material(s). In addition, the use of such methods could increase the likelihood of reducing a fractured region of bone (or other anatomical structure) by weakening healed and/or healthy bone and/or connective tissues along desired fracture lines, allowing the expansion of the filling member (and/or use of associated surgical devices such as tamps, etc) to displace some or all of the surrounding bony materials to a desired anatomical position.

Various of types of all these described surgical tools could include, but are not limited to, balloons and tools used for creating and filling voids in bone, mechanical cavity creation devices and vertebroplasty filling tools, energy-emitting tools for creating cavities, and/or mechanical cavity creation devices and high-pressure injection devices, which are disclosed in U.S. Pat. Nos. 5,108,404; 6,726,691; 6,676,665; 6,355,032; 7,097,648 and U.S. Patent Application No. US 200610079905; the disclosures of which are all incorporated herein by reference.

In various described embodiments, the surgical tools used in conjunction for altering the size and/or configuration of the cavity could comprise any and/or all of the above described instruments, utilized in conjunction with each other as well as one or more filling members, as disclosed herein. If desired, the filling member(s) could be utilized at virtually any point in a surgical procedure (including prior to introduction, during expansion and/or after removal of the filling member) to create, enlarge, reduce and/or modify the dimensions of the opening, recess and/or cavity, either in conjunction with or in place of the previously-described surgical tools and/or techniques.

For example, after cavity formation and removal of various surgical instruments, the filler member could be introduced to fill the cavity. If desired, the filler member could be inflated to sufficient pressures and/or expanded to sufficient size and/or dimensions to further compress and/or manipulate the surrounding cancellous and/or cortical bone (or other surrounding material), thereby altering the dimensions of the surrounding cavity. If desired, additional surgical devices could be introduced at any point in the procedure (including during introduction of the medicine into the filling member) to modify bone or connective tissues along desired fracture planes to induce desirable movement and/or reduction of fractures. In addition, it should be understood that the filling member could be removed during surgery (after introduction of an amount of medical material through the filling member in the previously described manner) to accommodate other surgical instruments to modify the cavity, bone, connective tissues and/or the implanted medical material, before reintroduction of the filling member and subsequent introduction of additional materials, if desired.

In various embodiments, the disclosed tools and techniques could be utilized through a single or multiple access paths, either consecutively or concurrently. For example, where an access path is established through both of the pedicles of a single vertebral body, one or more of the tools described herein could be utilized through one path through one pedicle, while the same or a different surgical tool could be utilized through another path through the second pedicle. If desired, both tools could be utilized within the same or different cavities/regions within the targeted anatomical region.

The filler material will desirably comprise a material that can be introduced into the cavity, but which in various embodiments will resist extravasation out of the cavity and/or vertebral body when the filling member is removed from the cavity. For example, the ingredients of the filler material could be specifically tailored such that the material can easily be introduced into the filling member, but then which subsequently cures and/or hardens. If desired, the curing and/or hardening of the filling material could be accelerated (by applying heat, for example) or curing and/or hardening of the filling material could be retarded (by cooling, for example). If desired, an expandable structure, such as a stent, could be introduced into the filling member. If desired, the filling material could comprise a material having particles generally larger than pores in the filling member. In a further embodiment, the particles of the filling material could be generally larger than the average pore size within the cancellous bone. In another embodiment, the filling material could comprise a settable material, such as a two-part polyurethane material or other curable biomaterial. In various alternative embodiments, the filling member could comprise a bioabsorbable material and/or fabric/mesh material as the structure.

If desired, the filling member can be designed to assume a predetermined shape and/or size, such as where the filling/stabilizing material will desirably cure into the shape of the surrounding filling member and/or the shape of the surrounding passage and/or the shape of a surrounding opening and/or osteotomy plane (i.e., the filling/stabilizing material could assume the shape of one, two or all three surrounding environments, or any combination thereof) within the vertebral body. In addition, the filling member may have a manipulatable tip (i.e., a directable tip such as the tip of a bronchoscope) or other section (i.e., a curved internal stylet, etc.) that allows the filling member to be positioned in a desired orientation relative to the cannula and/or the targeted anatomical region.

By filling the filling member in the cavity with the filling/stabilizing material, and then removing the filling member after the material has increased in viscosity and/or flow resistance, the filling member desirably provides a barrier to reduce, limit, control and/or prevent leakage or egress of the filling/stabilizing material, its components, intermediate products and/or any other introduced materials and/or additives, within the vertebral body. This may eliminate, reduce and/or prevent the emission of materials into the patient's body, materials which could cause and/or lead to hypotension, toxemia, emboli and/or thrombus outside of the carefully delineated cavity—all factors of which can ultimately can cause death. Moreover, the use of a removable filling member to assist in the delivery of the filling/stabilizing material desirably isolates (either partially and/or fully) the filling/stabilizing material(s), its components, intermediary products, by-products, and/or end products from the surrounding treated vertebral body and/or the remainder of the patients body. The present invention, therefore, allows the use of implant materials that heretofore were not well-suited and/or safe for implantation.

For example, where the patient is especially susceptible to the effects of a component and/or intermediate product of the filler/stabilizing material, 30 such as the cardiac depressive effects of the monomer component of PMMA, the use of a removable filling member to isolate (or suspend, delay or reduce the effects of) the unpolymerized monomer from the patient's vascular system until substantial completion of polymerization significantly reduces the concentration and/or total amount of monomer traveling into the patient's system. Once polymerization (or other appropriate chemical reaction) is complete, and the amount of free monomer is significantly reduced, any remaining material (i.e., free monomer) can be drawn and/or aspirated out through the guide tube of the filling member (or may be neutralized through the introduction of other chemicals, etc.) prior to release of the closure and removal of the filling member, or any residual monomer may remain within the filling member and be allowed to simply enter the patient's system, at the physician's option. Moreover, removal of the filling member can be staged (or slowed) to reduce the initial "burst" or increased concentration (i.e., "peak") of free monomer released into the patient's system. In a similar manner, the intermediate products of certain types of injectable and polymerizable polymers that can be hazardous to patients are isolated, while the end products of such polymerization are harmless. Alternatively, additional saline or other material could be introduced into the filling member to aspirate and/or dilute the concentration of the material.

The filling/stabilizing material can comprise a flowable material which is capable of setting to a less-flowable and/or hardened condition, such as bone cement, allograft tissue, autograft tissue, a remodelable material (such as Norian SRS material), resorbable materials such as calcium phosphate, hydroxyapatite, and/or synthetic bone substitute. In a preferred embodiment, the filler/stabilizing material can comprise any material capable of being introduced into the cavity through the delivery cannula and that sets to a generally hardened or less-flowable condition. As previously noted, various types of materials could also be "compressed" into a more solid shape, such as by using a vacuum draw on the filling member, if desired.

In various embodiments, the filler/stabilizing material can comprise a compression-resistant material, such as rubber, polyurethane, cyanoacrylate, or silicone rubber, which is inserted into the cavity in a flowable or semi-flowable state. The filler/stabilizing material can also comprise a semi-solid slurry material (e.g. a bone slurry in a saline base), which is either contained within a porous fabric structure located in the cavity or injected directly into the cavity, to resist compressive forces within the cavity.

If desired, the filling member could further comprise (or contain or be contained within) a stent, reinforcing bar (rebar) or other types of internal support structure, which desirably resist compressive, tensile, torsional and/or shear forces acting on the bone and/or filler/stabilizing material. The filler/stabilizing material could comprise a medication, or a combination of a medication and a compression-resistant material, as described above. Alternatively, the filler/stabilizing material can comprise a bone filler/stabilizing material which does not withstand a significant amount of compressive, tensile, torsional and/or shear forces within the cavity. For example, where the patient is not expected to experience significant forces within the spine immediately after surgery, such as where the patient is confined to bed rest or wears a brace, the filler/stabilizing material need not be able to immediately bear loads. Rather, the filling/stabilizing material could provide a scaffold for bone growth, or could comprise a material which facilitates or accelerates bone growth, allowing the bone to heal over a period of time. As another alternative, the stabilizing material could comprise a resorbable or partially resorbable source of organic or inorganic material for the treatment of various bone or non-bone-related disorders including, but not limited to osteoporosis, cancer, degenerative disk disease, heart disease, acquired immune deficiency syndrome (AIDS) or diabetes. In this embodiment, the cavity and/or stabilizing material could comprise a source of material for treatment of disorders located remotely from the cavity, to include disorders located outside the treated bone.

In an alternative embodiment, following expansion of the filling member, some or all of the filling member could be left in the cavity as a temporary or permanent scaffold or containment filling member of the filling/stabilizing material. In this arrangement, flowable filling/stabilizing material is conveyed into and/or around the filling member which serves to contain the material. The filling member, filled with and/or surrounded by the material, serves to provide augmented interior structural support function for the cortical bone. In addition to avoiding such potential for unsupported or partially-supported collapse of the cavity, the presence of such support materials reduce or eliminates the opportunity (prevalent in prior art tools and techniques) for fluids and/or other tissues to invade the cavity after removal of the expansion member but prior to introduction of the filling material.

In various embodiments, the filling/stabilizing material will serve as the expansion medium for the filling member to compact cancellous bone and form the cavity, to thereby perform both cavity creation/bony reduction and interior support/stabilization functions. Alternatively, the structure can be first expanded with another medium (such as a medium particularly well suited to the transfer of hydrostatic forces—i.e. a liquid or saline solution) to compact cancellous bone and/or reduce the bone (thereby forming the cavity), and the filling/stabilizing material can be subsequently introduced after the expansion medium is removed from the structure to provide the interior support/stabilization structure. As another alternative, the filling/stabilizing material could comprise a two-part material including, but not limited to, settable polymers or calcium alginate. If desired, one part of the filling/stabilizing material could be utilized as the expansion medium, and the second part added after the desired cavity size is achieved. Reduction of the vertebral body is monitored by the surgeon observing the placement of the stabilizing material by x-ray or other minimally and/or non-invasive methods. When reduction has been achieved, the delivery of additional volume of filling/stabilizing material may be terminated (or may be continued, at the physician's option and desired outcome).

Alternative Embodiments

FIG. 9a through 9f depict one alternative embodiment of a surgical tool 1500 incorporating a filling control device or member constructed in accordance with various teachings of the present invention. In this embodiment, the surgical tool 1500 comprises a longitudinally-extending central body 1510 having a proximal end 1520 and a distal end 1530, with a lumen 1540 extending longitudinally there through. A quick-release Y-type fitting 1550 with a sealing cap 1555 is attached to the proximal end 1520. An extraction assembly 1560 is positioned about the central body 1510, the assembly 1560 having a longitudinally-extending outer sheath 1570 connected near its proximal end 1580 to an extraction collar 1590. The outer sheath 1570, having a proximal end 1580 and a distal end 1585, incorporates a series of extraction threads 1600 at the proximal end 1580, surrounded by an extraction collar 1610 having an internally-threaded mating section 1620 surrounding and engaging with the extraction threads 1600. The extraction assembly further comprises an sheath advancement/withdrawal mechanism 1625. A filling control member 1630 is secured to the distal end 1530 of the central body. 1510. One or more threads or release members 1640 extend from a releasable aperture 1650 of the filling control member 1630, through the lumen 1540 and are attached to the sealing cap 1555.

The surgical tool 1500 is prepared for use by manipulating the sheath advancement/withdrawal mechanism 1625 to initially advancing the distal end 1585 of the sheath 1570 towards and over the filling control member 1630, desirably encasing and/or compressing some and/or all of the member 1630 with the sheath 1570. The distal end of the tool 1500 and sheath 1570 are then advanced into and through the lumen 1650 of a standard surgical cannula 1660 that has desirably been placed through soft tissues and within a targeted anatomical region, such as into and/or through the pedicle of a targeted vertebral body (not shown). Desirably, the distal end of the tool 1500 will exit from the lumen 1650 and enter the targeted anatomical region, with the sheath protecting the filling control member 1630 from any surrounding anatomical structures (i.e., bone shards, etc) and guiding the member 1630 into a desired location. Once properly positioned, the sheath advancement/withdrawal mechanism 1625 is manipulated to withdraw the sheath 1570 and expose some or all of the filling control member 1630, desirably without displacing the member 1630 significantly. Once the sheath 1570 has been moved a sufficient amount (either partially or fully withdrawn away from the member 1630, at the physician's option), a source of medical or therapeutic material (not shown) can be attached to the Y-fitting 1550 and the material introduced through the lumen 1540 into the filling control member 1630.

Once a desired amount of medical or therapeutic material has been introduced into the filling control member 1630, the flow of material can interrupted, slowed and/or stopped. If the material experiences a phase or viscosity change over time (such as, for example, polymethymacrylate bone cement which polymerizes and/or hardens), the material can stay within the member 1630 (and isolated from the surrounding anatomy) until a desired consistency has been reached, and then the sealing cap 1555 can be removed, and the one or more release threads 1640 can be withdrawn from the filling member 1630, desirably opening the releasable aperture 1650. Once the aperture 1650 is opened, the extraction collar 1610 can be rotated using an attachable handle 1612, if desired, which in turn rotates the internally-threaded mating section 1620 against the extraction threads 1600, desirably converting the rotation force into a linear force, which withdraws the filling control member 1630 into the sheath 1570. Because the aperture 1650 is open, the member 1630 can be safely and efficiently withdrawn from the medical or therapeutic material, with little or no disruption to the material and/or the surrounding anatomical structures. Once the filling control member 1630 is drawn back into the sheath 1570, the tool 1500 is withdrawn from the cannula 1660 and the procedure completed.

The disclosed embodiment is especially well-suited to use during surgical procedures requiring a minimal surgical exposure, such as during a percutaneous or minimally-invasive surgical procedure. The disclosed embodiment is also especially well-suited for use near or within "sensitive" areas of a patient's anatomy, such as where unintended flow of therapeutic materials and/or its constituents or end products could cause considerable damage, such as in the spine or cranial cavity.

The present embodiment is also particularly well-suited for facilitate the release and withdrawal of the filling control member, even in the face of challenging anatomical conditions and/or the presence of medical or therapeutic material that hardens or thickens quickly and/or unexpectedly. Desirably, during withdrawal of the member 1630, the rotation of the extraction collar 1610 will desirably convert the rotational force imparted by the physician's hand to a linear force pulling the member 1630 away from the therapeutic or medical material and into the sheath 1570. Such force conversion can allow manual refraction of the member 1630 and/or sheath 1570 using the physician's finger strength rather than relying upon an additional tool to impart the necessary amount of force.

Figure 10A:
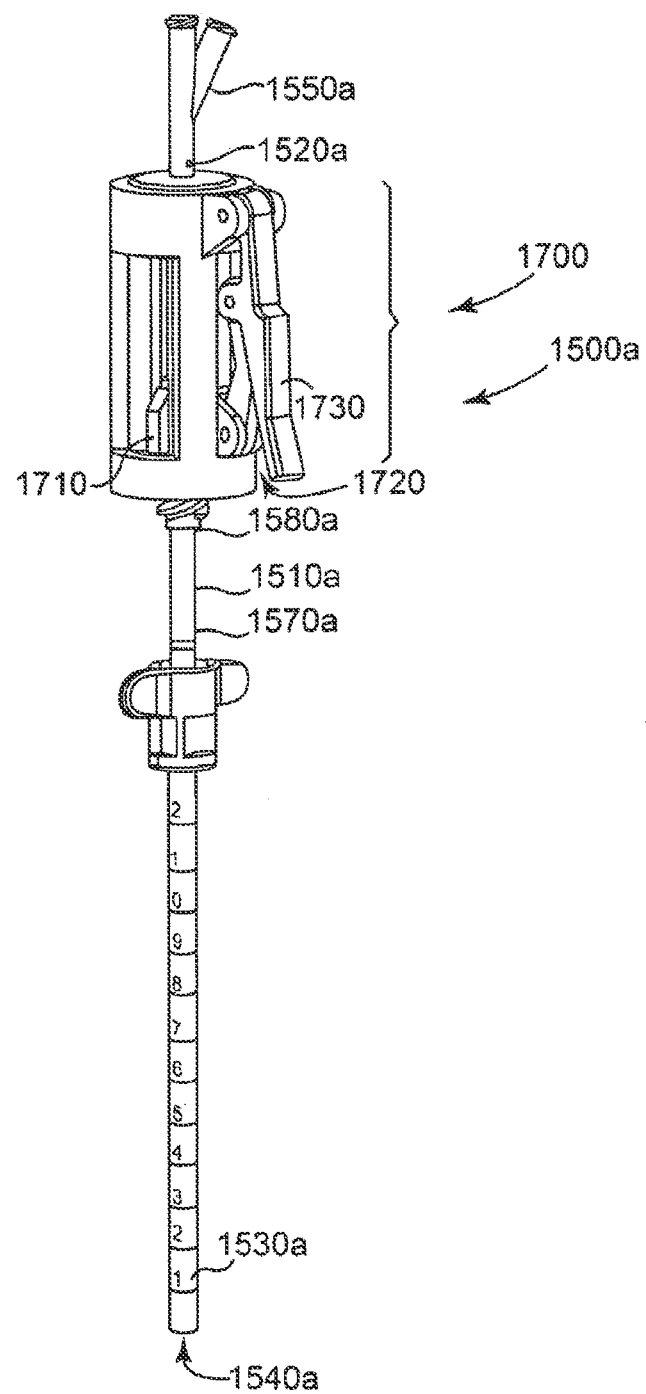
FIG. 10a is a perspective view of another alternate embodiment of a filling member constructed in accordance with the teachings of the present invention.
Figure 10B:
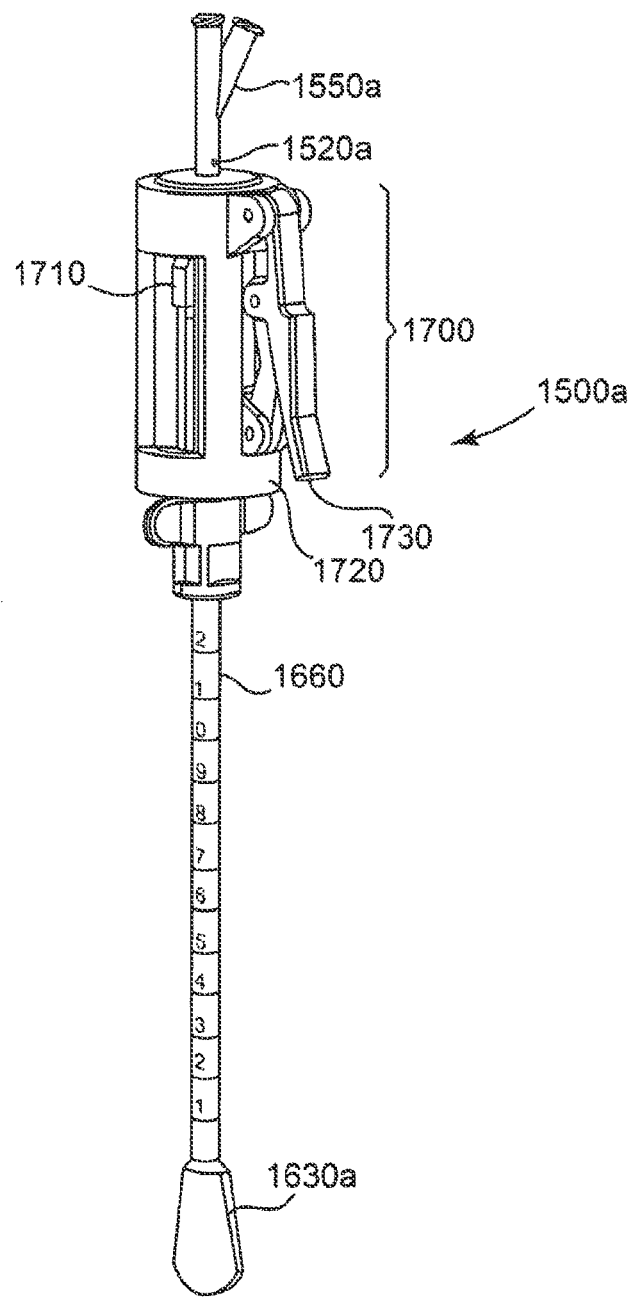
FIG. 10b is a perspective view of the filling member of FIG. 10a, depicting the sheath withdrawn from the filling member, and the filling member deployed and filled with a substance.
Figure 10C:
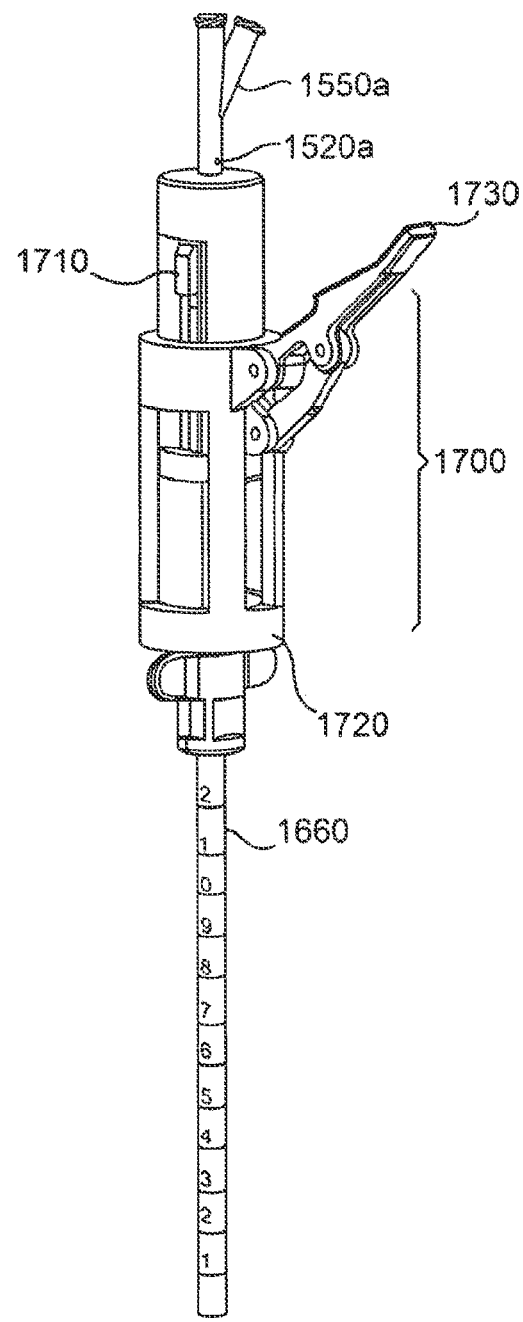
FIG. 10c is a perspective view of the filling member of FIG. 10a, with the filling member withdrawn into the sheath.

FIGS. 10a through 10c depict one alternative embodiment of a surgical tool 1500a incorporating a filling control device or member constructed in accordance with various teachings of the present invention. Because many of the components and featured of the present embodiment are the same or similar to those described in connection with the previous embodiment, like reference numerals will be used to denoted the same or similar components.

In this embodiment, the surgical tool 1500a comprises a longitudinally-extending central body 1510a having a proximal end 1520a and a distal end 1530a, with a lumen 1540a extending longitudinally there through. A quick-release Y-type fitting 1550a is attached to the proximal end 1520a. A sheath advancement/withdrawal mechanism 1700 is positioned about the central body 1510a. The mechanism 1700 comprises a longitudinally-extending outer sheath 1570a connected near its proximal end 1580a to a sliding actuator 1710 positioned with an extractor collar 1720. The sliding actuator 1710 is desirably slidably secured within the collar 1720, whereby longitudinal movement of the sliding actuator 1710 results in longitudinal movement of the sheath 1570a relative to the collar 1720. The mechanism 1700 further comprises an extraction lever 1730 secured to the collar 1720, with the lever 1730 further attached to the central body 1510a such that movement of the lever 1730 results in longitudinal movement of the central body 1510a relative to the collar 1720. If desired, the position of the sliding actuator 1710 can be utilized by the physician as an indicator of the orientation of the filling member or other component(s) of the tool which are not readily observable during the surgical procedure.

In use, the sliding actuator 1710 is advanced towards the distal end 1530*a* of the central body 1510*a*, resulting in the sheath 1570*a* traveling over and encasing, compressing and/or enclosing the member 1630*a*. The distal end of the tool 1500*a* and surrounding sheath 1570*a* are then advanced into and through the lumen (not shown) of a standard surgical cannula 1660 has desirably been placed through soft tissues and within a targeted anatomical region, such as into and/or through the pedicle of a targeted vertebral body. Desirably, the distal end of the tool 1500*a* will exit from the cannula lumen and enter the targeted anatomical region, with the sheath 1570*a* protecting the filling control member 1630*a* from any surrounding anatomical structures (i.e., bone shards, etc) and guiding the member 1630*a* into a desired location. Once properly positioned, the sliding actuator 1710 is withdrawn away from the distal end 1530*a* of the central body 1510*a*, desirably exposing some or all of the filling control member 1630*a*, desirably without displacing the member 1630*a* significantly or in an undesired manner. Once the sheath 1570*a* has been moved a sufficient amount (either partially or fully withdrawn away from the member 1630*a*, at the physician's option), a source of medical or therapeutic material (not shown) can be attached to the Y-fitting 1550*a* and the material introduced through the lumen into the filling control member 1630*a*.

Once a desired amount of medical or therapeutic material has been introduced into the filling control member 1630*a*, the flow of material can interrupted, slowed and/or stopped. If the material experiences a phase or viscosity change over time (such as, for example, polymethymacrylate bone cement which polymerizes and/or hardens), the material can stay within the member 1630*a* (and isolated from the surrounding anatomy) until a desired consistency has been reached, and then the member 1630*a* can be opened as previously described. Once the member is opened a desired amount, the extraction lever 1730 can be actuated, desirably withdrawing the central body 1510*a* from the material and back towards and/or within the sheath 1570*a*. Because the member is open, the member 1630*a* can be safely and efficiently withdrawn from the medical or therapeutic material, with little or no disruption to the material and/or the surrounding anatomical structures. Once the filling control member 1630*a* is drawn back into the sheath 1570*a*, the tool 1500*a* is withdrawn from the cannula and the procedure completed.

Figure 11A:
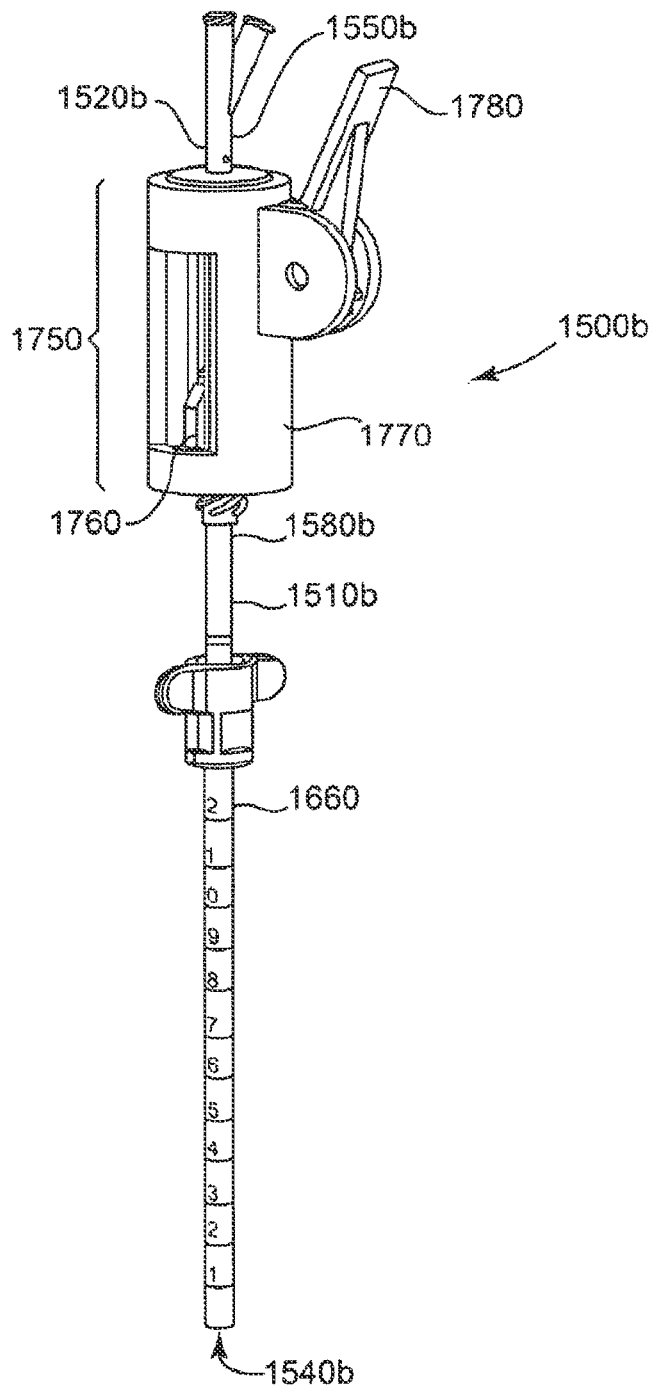
FIG. 11a is a perspective view of another alternate embodiment of a filling member constructed in accordance with the teachings of the present invention.
Figure 11B:
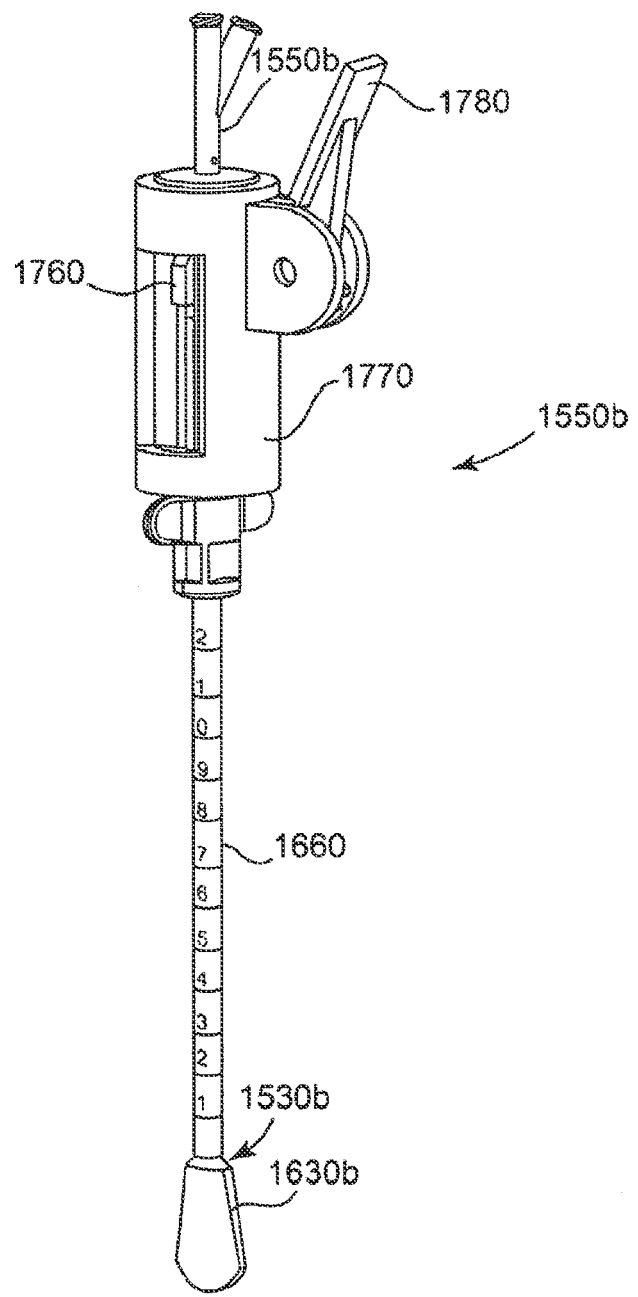
FIG. 11b is a perspective view of the filling member of FIG. 11a, depicting the sheath withdrawn from the filling member, and the filling member deployed and filled with a substance.
Figure 11C:
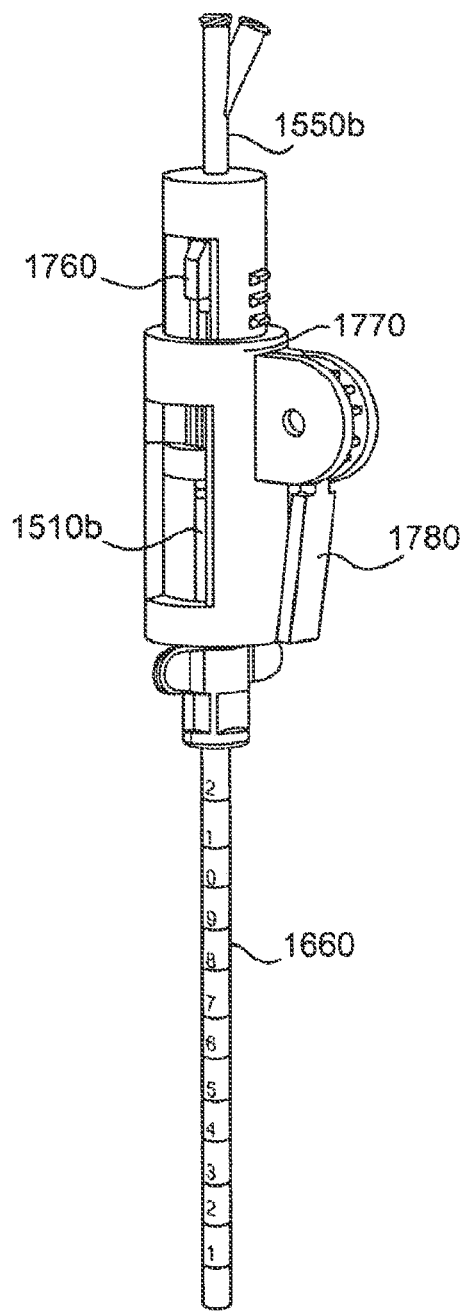
FIG. 11c is a perspective view of the filling member of FIG. 11a, with the filling member withdrawn into the sheath.
Figure 12A:
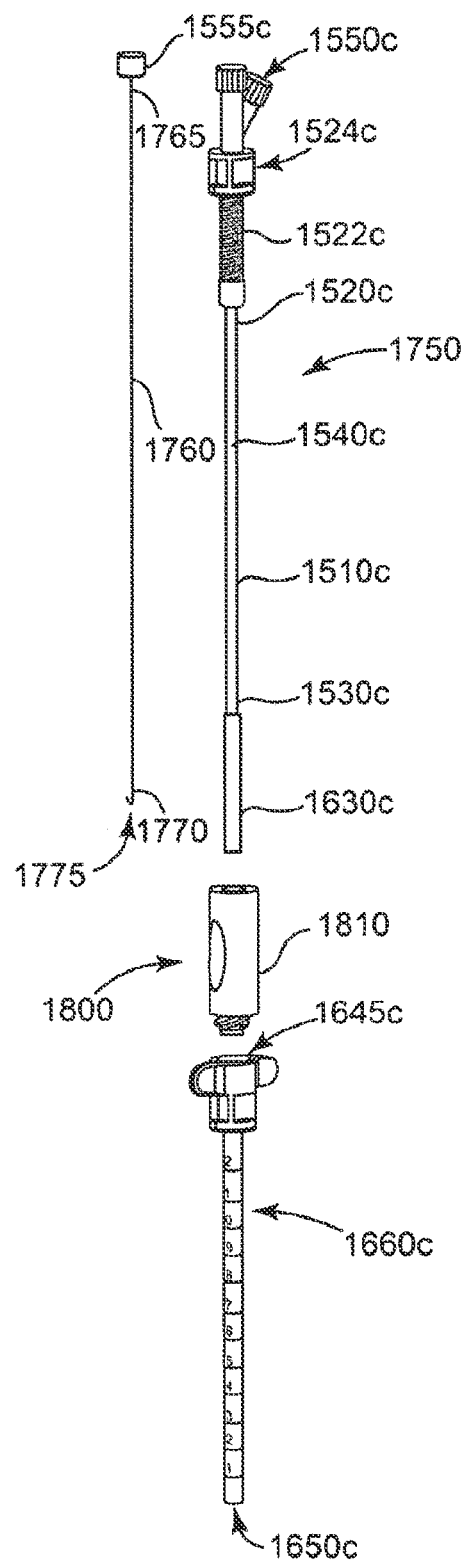
FIG. 12a is a perspective view of another alternate embodiment of a filling member constructed in accordance with the teachings of the present invention.
Figure 12B:
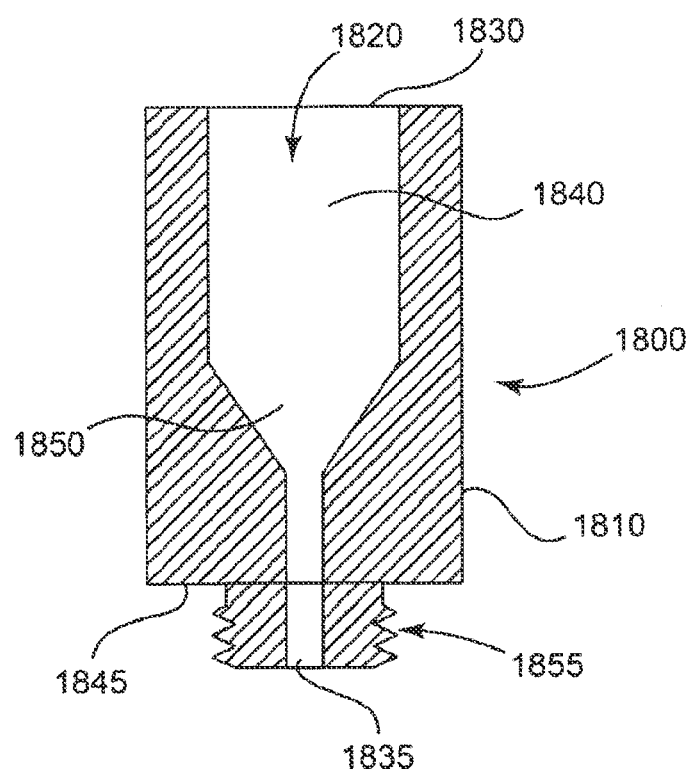
Figure 12C:
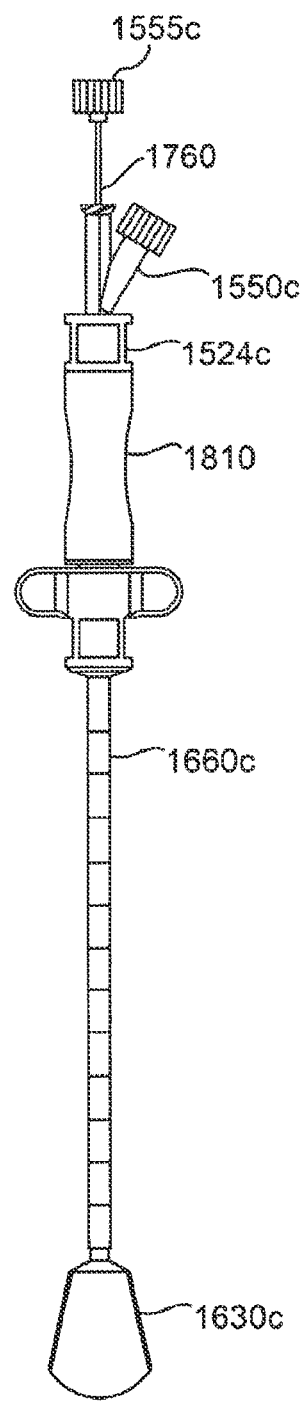
FIG. 12c is a perspective view of the filling member of FIG. 12a, depicting the filling member deployed and filled with a substance.
Figure 12D:
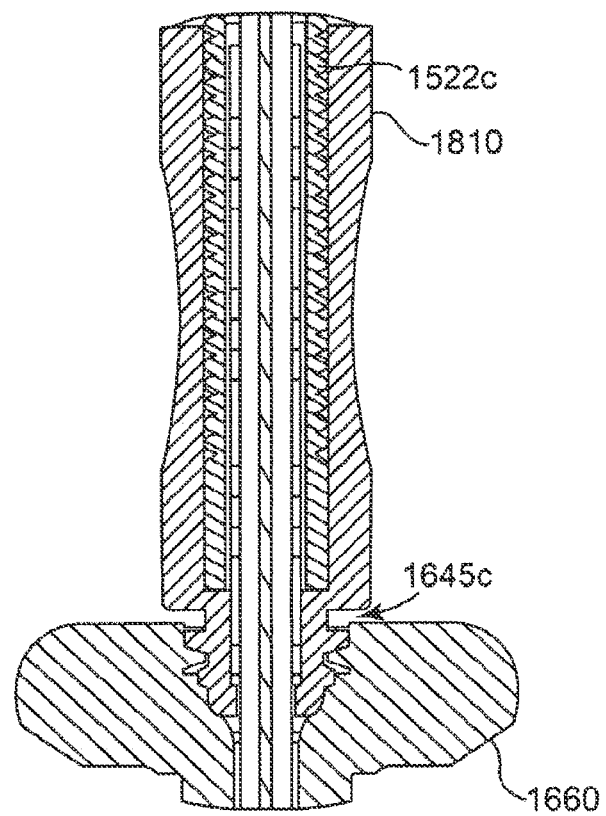
FIG. 12d is a longitudinal cross-sectional view of the locking arrangement between the compression fitting and the surgical cannula.
Figure 12E:
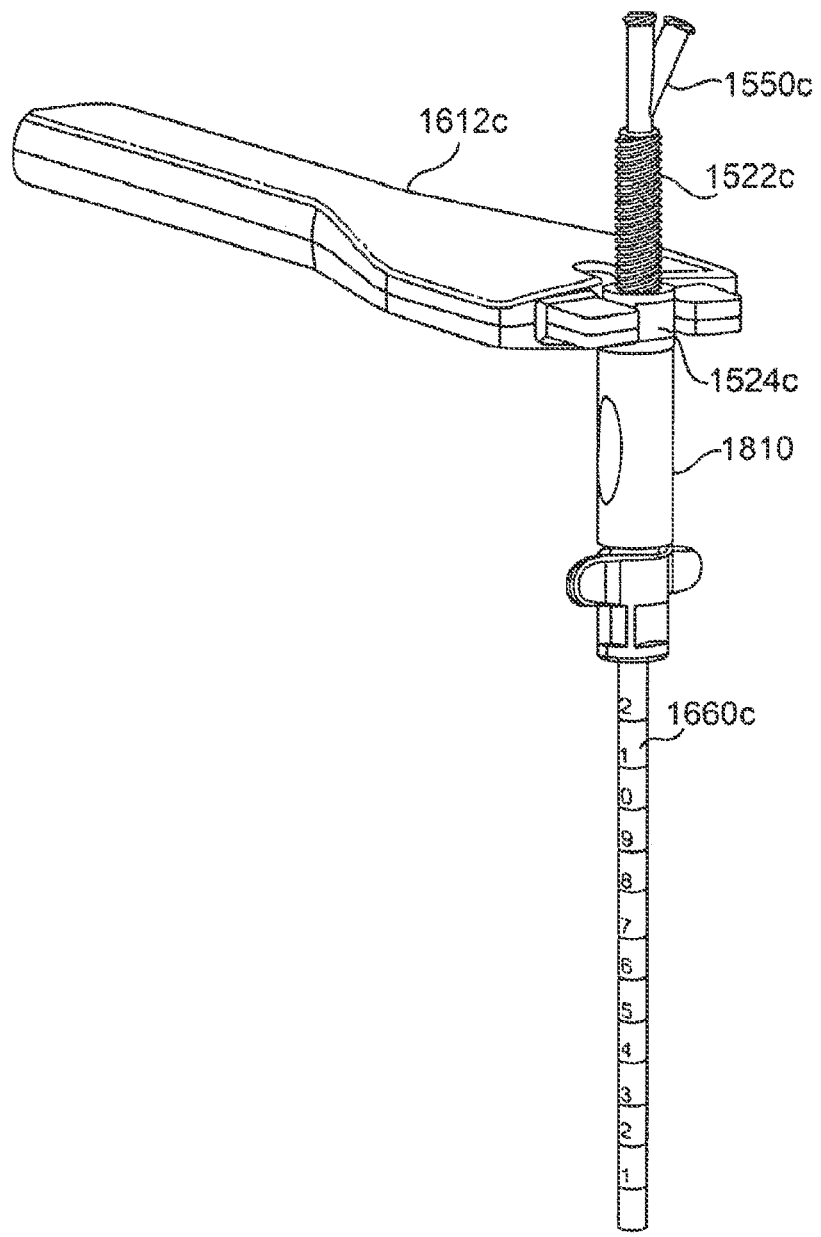
FIG. 12e is a perspective view of the filling member of FIG. 12a, with a rotatable arm connected to the withdrawal collar of the tool and depicting the filling member withdrawn into the cannula.

FIGS. 11*a* through 11*c* depict another alternative embodiment of a surgical tool 1500*b* incorporating a filling control device or member constructed in accordance with various teachings of the present invention. Because many of the components and featured of the present embodiment are the same or similar to those described in connection with the previous embodiment, like reference numerals will be used to denoted the same or similar components.

In this embodiment, the surgical tool 1500*b* comprises a longitudinally-extending central body 1510*b* having a proximal end 1520*b* and a distal end 1530*b*, with a lumen 1540*b* extending longitudinally there through. A quick-release Y-type fitting 1550*b* is attached to the proximal end 1520*b*. A sheath advancement/withdrawal mechanism 1750 is positioned about the central body 1510*b*. The mechanism 1750 comprises a longitudinally-extending outer sheath connected near its proximal end to a sliding actuator 1760 positioned with an extractor collar 1770. The sliding actuator 1760 is desirably slidably secured within the collar 1770, whereby longitudinal movement of the sliding actuator 1760 results in longitudinal movement of the sheath relative to the collar 1770. The mechanism 1750 further comprises an extraction lever 1780 (with pinion gears) secured to the collar 1770, with the lever 1780 further attached to the central body 1510*b* such that movement of the lever 1780 results in longitudinal movement of the central body 1510*b* relative to the collar 1770. If desired, the position of the sliding actuator 1760 can be utilized by the physician as an indicator of the orientation of the filling member or other component(s) of the tool which are not readily observable during the surgical procedure.

In use, the sliding actuator 1760 is advanced towards the distal end 1530*b* of the central body 1510*b*, resulting in the sheath traveling over and encasing, compressing and/or enclosing the member 1630*b*. The distal end of the tool 1500*b* and surrounding sheath are then advanced into and through the lumen (not shown) of a standard surgical cannula 1660 has desirably been placed through soft tissues and within a targeted anatomical region, such as into and/or through the pedicle of a targeted vertebral body. Desirably, the distal end of the tool 1500*b* will exit from the cannula lumen and enter the targeted anatomical region, with the sheath protecting the filling control member 1630*b* from any surrounding anatomical structures (i.e., bone shards, etc) and guiding the member 1630*b* into a desired location. Once properly positioned, the sliding actuator 1760 is withdrawn away from the distal end 1530*b* of the central body 1510*b*, desirably exposing some or all of the filling control member 1630*b*, desirably without displacing the member 1630*b* significantly or in an undesired manner. Once the sheath has been moved a sufficient amount (either partially or fully withdrawn away from the member 1630*b*, at the physician's option), a source of medical or therapeutic material (not shown) can be attached to the Y-type fitting 1550*b* and the material introduced through the lumen into the filling control member 1630*b*.

Once a desired amount of medical or therapeutic material has been introduced into the filling control member 1630*b*, the flow of material can interrupted, slowed and/or stopped. If the material experiences a phase or viscosity change over time (such as, for example, polymethymacrylate bone cement which polymerizes and/or hardens), the material can stay within the member 1630*b* (and isolated from the surrounding anatomy) until a desired consistency has been reached, and then the member 1630*b* can be opened as previously described. Once the member is opened a desired amount, the extraction lever 1780 can be actuated, desirably withdrawing the central body 1510*b* from the material and back towards and/or within the sheath. Because the member is open, the member 1630*b* can be safely and efficiently withdrawn from the medical or therapeutic material, with little or no disruption to the material and/or the surrounding anatomical structures. Once the filling control member 1630*b* is drawn back into the sheath, the tool 1500*b* is withdrawn from the cannula and the procedure completed.

FIGS. 12*a* through 12*e* depict another alternative embodiment of a surgical tool 1750, which incorporates a filling control device or member constructed in accordance with various teachings of the present invention. Because many of the components and featured of the present embodiment are the same or similar to those described in connection with the previous embodiment, like reference numerals will be used to denoted the same or similar components. In this embodiment, the surgical tool 1750 comprises a longitudinally-extending central body 1510*c* having a proximal end 1520*c* and a distal end 1530*c*, with a lumen 1540*c* extending longitudinally there through. A quick-release Y-type fitting 1550*c* is attached to the proximal end 1520*c* and a filling control member 1630*c* is attached to the distal end 1530*c*. A threaded withdrawal fitting 1522*c* is attached to the proximal end 1520*c*, with a rotating extraction collar 1524*c* having an internally-threaded section positioned about the withdrawal fitting 1522*c*, proximate the Y-type fitting 1550*c*.

The device further comprises a stylet 1760 or other type of stiffening component having a proximal end 1765 and a distal end 1770. A luer cap 1555*c* is attached to the proximal end 1765 of the stylet 1760, with the distal end 1770 of the stylet 1760 having a blunt or otherwise textured tip 1775 (i.e., a curved or "bent-over" tip). If desired, the stylet and/or tip may comprise a radiopaque material to indicate the position, location and/or orientation of the stylet/filling member within the targeted anatomical region.

Desirably, the stylet 1760 is sized and configured to pass through the lumen 1540*c* and into the member 1630*c*, thereby imparting some level of stiffness to the otherwise flexible member 1630*c*, yet without perforating or otherwise violating the structural integrity of the flexible wall of the member 1630*c*. In addition, it is desired that one or more actuating devices or wires (not shown), such as the release threads as described in conjunction with the embodiment of FIG. 10, be capable of passing through the lumen coincident with the stylet 1760. If desired, the stylet 1760 may be of a sufficient length to extend the member 1630*c* to its fullest extent, or the stylet may be longer if stretching the member 1630*c* is desired, or the stylet may be shorter than the full length of the tool 1750 if full extension of the member 1630*c* is not desired.

The tool 1750 further comprises a compression fitting 1800 having a cylindrical body 1810 with a lumen 1820 extending longitudinally there through, the cylindrical body 1810 having a proximal end 1830 and a distal end 1835, with the lumen 1820 having a larger diameter section 1840 adjacent the proximal end 1830 and a reduced diameter section 1845 adjacent the distal end 1835, and a tapered section 1850 there between. A series of luer threads 1855, or other securable fitting, is positioned adjacent the distal end 1835 of the fitting 1800.

In use, the tool 1750 is prepared for introduction by first sliding the stylet 1760 into the lumen 1540*c* of the tool 1750, with the luer cap 1555*c* secured to the corresponding threads of the Y-type fitting 1550*c*. Desirably, this will cause the distal tip 1775 of the stylet 1760 to contact the member 1630*c*, and potentially stiffening or stretching the member 1630*c* and thereby desirably reducing its cross-sectional profile. The member 1630*c* and stylet 1630*c* are then inserted into the larger diameter section 1840 of the lumen 1820 of the compression fitting 1800. The member 1630*c* and stylet 1760 are then progressively inserted into and through the tapered section 1850 and into the reduced diameter section 1845 of the compression fitting.

The compression fitting 1800 is secured via the luer threads 1855 to a corresponding luer fitting 1645*c* of a standard surgical cannula 1660*c* that has desirably been placed through soft tissues and within a targeted anatomical region, such as into and/or through the pedicle of a targeted vertebral body (not shown). Desirably, the lumen 1650*c* of the cannula 1660*c* is approximately the same cross-sectional diameter, shape and size as the reduced diameter section 1845 of the lumen 1820. Once the compression fitting 1800 is secured to the cannula 1660*c*, the member 1630*c* and stylet 1760 (as well as the remainder of the tool 1750) can be advanced through the lumen 1650*c* of the cannula 1660*c* and into a targeted anatomical region. Desirably, the presence of the lumen facilitates the passage and advancement of the member 1630*c* to a desired location and/or position/orientation. In one desired embodiment, the tool 1750 is advanced through the cannula 1660*c*, with the threaded withdrawal fitting 1522*c* passing at least partially within the larger diameter section 1840 of the cylindrical body 1810 until the rotating extraction collar 1524*c* abuts against the proximal end 1830 of the cylindrical body 1810.

Once the member 1630*c* has been properly positioned and, if desired, the position/orientation of the stylet and surrounding filing member had been verified fluoroscopically, the luer cap 1555*c* can be released and the attached stylet 1760 withdrawn from the member 1630*c* and the lumen 1540*c* of the tool 1750. A source of medical or therapeutic material (as previously noted and described) can be attached to the Y-fitting 1550*c* and the material introduced through the lumen 1540*c* into the filling control member 1630*c*.

Once a desired amount of medical or therapeutic material has been introduced into the filling control member 1630*c*, the flow of material can interrupted, slowed and/or stopped. If the material experiences a phase or viscosity change over time (such as, for example, polymethymacrylate bone cement which polymerizes and/or hardens), the material can stay within the member 1630*c* (and isolated from the surrounding anatomy) until a desired consistency has been reached, and then the member 1630*c* can be opened as previously described in conjunction with various of the other disclosed embodiments. Once the member is opened a desired amount, the rotating extraction collar 1524*c* can be rotated in a desired direction, which desirably withdraws the central body 1510*c* from the material and back towards and/or within the cannula 1660*c*. If desired, a removable handle 1612*c* can be utilized to engaged with and assist in rotation of the collar 1524*c*. Because the member 1630*c* is open at this point, the member 1630*c* can be safely and efficiently withdrawn from the medical or therapeutic material, with little or no disruption to the material and/or the surrounding anatomical structures. Once the filling control member 1630*c* is completely drawn back into the cannula 1660*c*, the tool 1750 can be withdrawn from the cannula and the procedure completed.

Figure 13A:
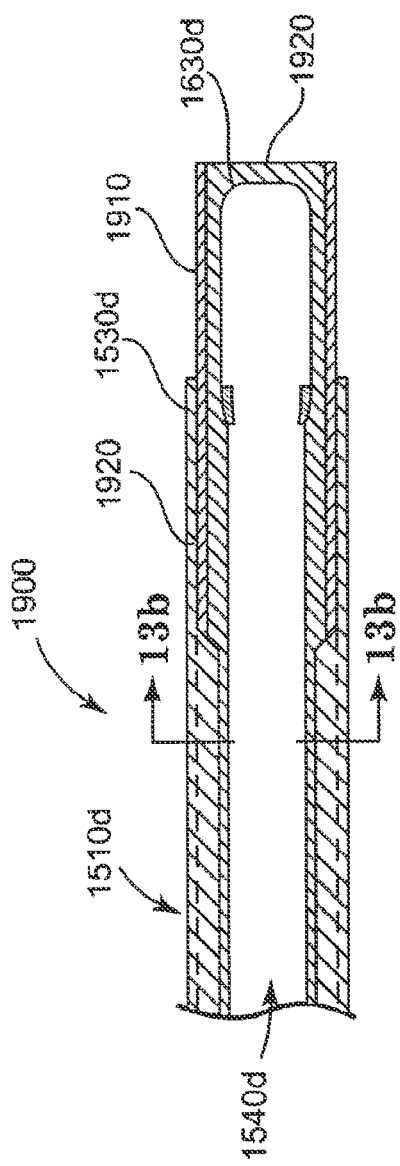
FIG. 13a is a partial longitudinal cross-sectional view of another alternate embodiment of a filling member constructed in accordance with the teachings of the present invention.
Figure 13C:
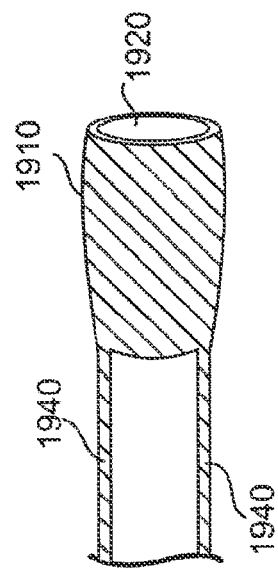
Figure 13B:
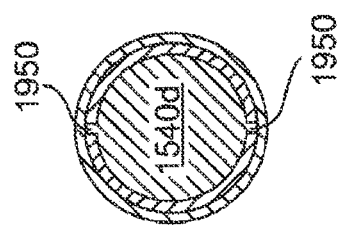
FIG. 13b is a cutaway cross-sectional view of the filling member of FIG. 13a, along line 13b-13b.

FIGS. 13*a* through 13*c* depict another alternative embodiment of a surgical tool 1900, which incorporates a filling control device or member constructed in accordance with various teachings of the present invention. Because many of the components and featured of the present embodiment are the same or similar to those described in connection with the previous embodiment, like reference numerals will be used to denoted the same or similar components. In this embodiment, the surgical tool 1900 comprises a longitudinally-extending central body 1510*d* having a distal end 1530*d*, with a lumen 1540*d* extending longitudinally there through. A filling control member 1630*d* is attached to the distal end 1530*d*.

In this embodiment, the distal end 1530*d* of the tool 1900 further incorporates a telescoping sheath 1910 which extends from the lumen 1540*d* of the tool 1900. Desirably, the sheath 1910 is sized to pass within an enlarged diameter section 1920 proximate the distal end 1530*d* of the tool 1900, and the sheath 1910 further has a sheath lumen 1920 sized to accommodate the filling control member 1630*d* in a compacted state. During use, the sheath 1920 will protect and secure the filling member 1630*d* during introduction of the tool into the targeted anatomical space. Once in position, the sheath can be withdrawn into the distal end 1530*d* by pulling or drawing on the withdrawal members 1940 attached to the sheath 1920, desirably withdrawing the sheath back into the enlarged diameter section 1920, and exposing some or all of the filling member. Once the sheath is fully refracted, a filling material can be introduced into the filling member in the previously-described manner.

Once a desired amount of material has been introduced, an openable closure (not shown) in the filling member can be opened, and the filling member withdrawn from the filler material as previously described. This withdrawal can be accomplished by withdrawing the catheter back through the catheter lumen, pulling the filling member away from the material and drawing it back into the sheath lumen and catheter lumen. Once withdrawn a desired distance, the tool can be removed In this embodiment, the withdrawal members 1640 will desirably travel in slots 1950 formed in the walls of the lumen 1540d. Such an arrangement allows the wall thickness of the catheter to be minimized while maintaining sufficient lumen size to allow passage of the catheter as well filling material and one or more release mechanisms for actuating the openable closure of the filler member, while providing for a sheath to protect and compress the filling member as desired during the surgical procedure.

FIGS. 14a through 14g depict another alternative embodiment of a surgical tool 2000, which incorporates a filling control device or member constructed in accordance with various teachings of the present invention. Because many of the components and featured of the present embodiment are the same or similar to those described in connection with the previous embodiment, like reference numerals will be used to denoted the same or similar components.

In this embodiment, the surgical tool 2000 comprises a longitudinally-extending central body 1510e having a proximal end 1520e and a distal end 1530e, with a lumen 1540e extending longitudinally there through. A quick-release Y-type fitting 1550e is attached to the proximal end 1520e. A sheath advancement/withdrawal mechanism 2010 is positioned about the central body 1510e. The mechanism 2010 comprises a longitudinally-extending outer sheath 2020 connected near its proximal end to a sliding actuator 2030 positioned within an extractor collar 2040. The sliding actuator 2030 is desirably slidably secured within the collar 2040, whereby longitudinal movement of the sliding actuator 2030 results in longitudinal movement of the sheath relative to the collar 2040. In this embodiment, the actuator 2030 desirably extends outwards of the collar 2040, desirably making it easier for an operator to touch and operate the actuator 2030, as desired. The mechanism 2010 further comprises an actuation nut 2050 secured to the collar 1770 (i.e., via a rotatable snap fit, etc.), with the nut 2050 having internally extending threads 2060 which engage with external threads 2070 attached to the central body 1510b, the threads 2060 and 2070 engaging such that rotation of the nut 2050 results in longitudinal movement of the central body 1510e relative to the collar 2040. If desired, the position of the sliding actuator 2030 can be utilized by the physician as an indicator of the orientation of the filling member or other component(s) of the tool which are not readily observable during the surgical procedure.

In use, the sliding actuator 2030 is advanced along a guidance slot 2080 towards the distal end 1530e of the central body 1510e, resulting in the sheath traveling over and encasing, compressing and/or enclosing the member 1630e. See FIG. 14d. If desired, the actuator 2030 may be placed in a notch 2095 or other locking mechanism to prevent unwanted movement during manipulation of the tool 2000. The distal end 1530e of the tool 2000 and surrounding sheath are then advanced into and through the lumen (not shown) of a standard surgical cannula 1660 has desirably been placed through soft tissues and within a targeted anatomical region, such as into and/or through the pedicle of a targeted vertebral body. If desired, the tool 2000 can be connected to the cannula 1660 using a series of luer threads 2090 which engage with corresponding threads (not shown) on the cannula. See FIG. 14e. Desirably, the distal end 1530e of the tool 2000 will exit from the interior lumen of the cannula and enter the targeted anatomical region (not shown), with the sheath protecting the filling control member 1630e from any surrounding anatomical structures (i.e., bone shards, etc) and guiding the member 1630e into a desired location. Once properly positioned, the sliding actuator 2030 is rotated and drawn away from the distal end 1530e of the central body 1510e, traveling along the slot 2080 and desirably exposing some or all of the filling control member 1630e, desirably without displacing the member 1630e significantly or in an undesired manner. See FIG. 14F. If desired, the sliding actuator may be rotated into a corresponding notch (not shown) at the far end of the slot 2080, to prevent unwanted movement during manipulation of the tool 2000. Once the sheath has been moved a sufficient amount (either partially or fully withdrawn away from the member 1630e, at the physician's option), a source of medical or therapeutic material (not shown) can be attached to the y-fitting 1550e and the material introduced through the lumen into the filling control member 1630e. See FIG. 14f.

Once a desired amount of medical or therapeutic material has been introduced into the filling control member 1630e, the flow of material can interrupted, slowed and/or stopped. If the material experiences a phase or viscosity change over time (such as, for example, polymethymacrylate bone cement which polymerizes and/or hardens), the material can stay within the member 1630e (and isolated from the surrounding anatomy) until a desired consistency has been reached, and then the member 1630e can be opened as previously described. Once the member is opened a desired amount, the nut 2050 can be rotated, desirably withdrawing the central body 1510e from the material and back towards and/or within the sheath 2020. Because the member is open, the member 1630e can be safely and efficiently withdrawn from the medical or therapeutic material, with little or no disruption to the material and/or the surrounding anatomical structures. Once the filling control member 1630e is drawn back into the sheath (See FIG. 14g), the tool 2000 is disengaged from and withdrawn from the cannula 1660 and the procedure completed.

Figure 15:
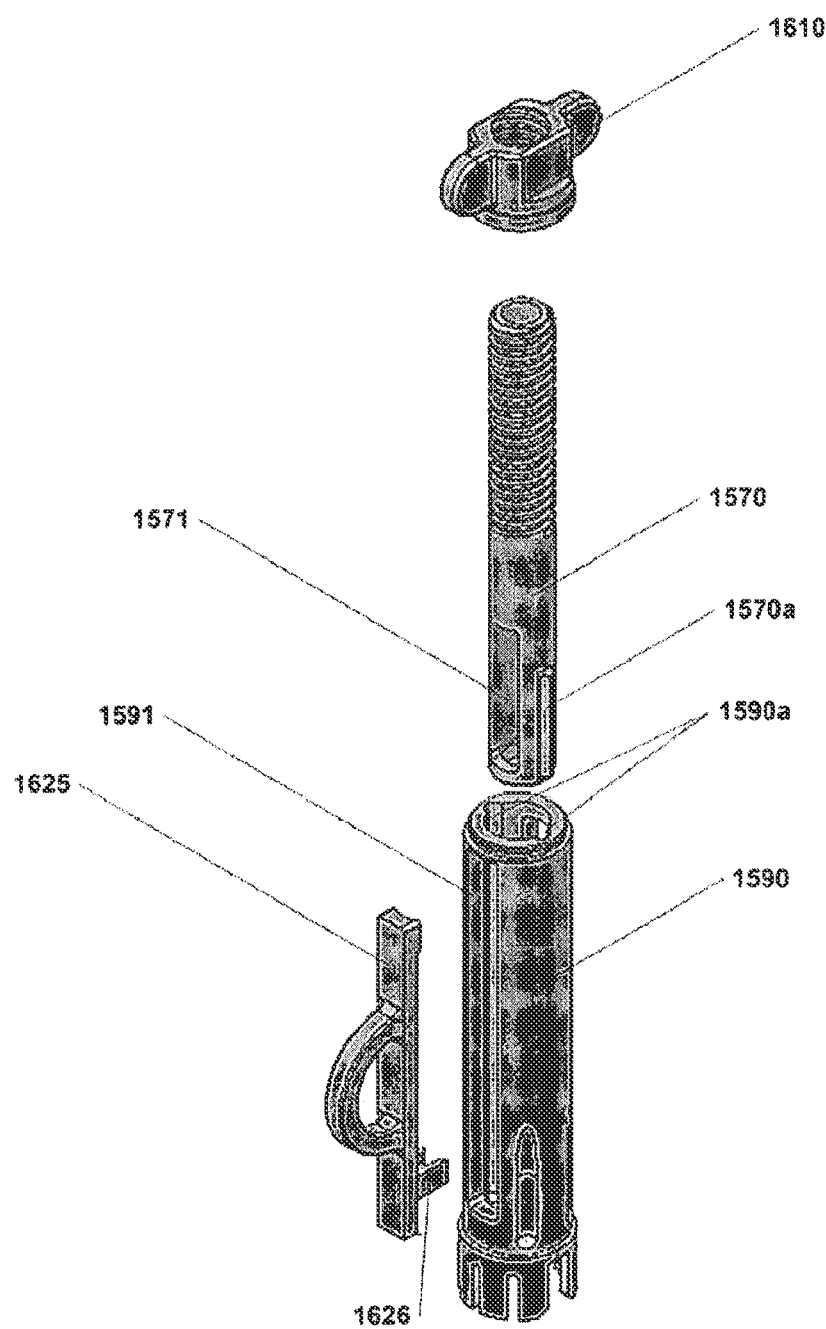
FIG. 15 is a perspective exploded view of certain components of another embodiment.
Figure 16:
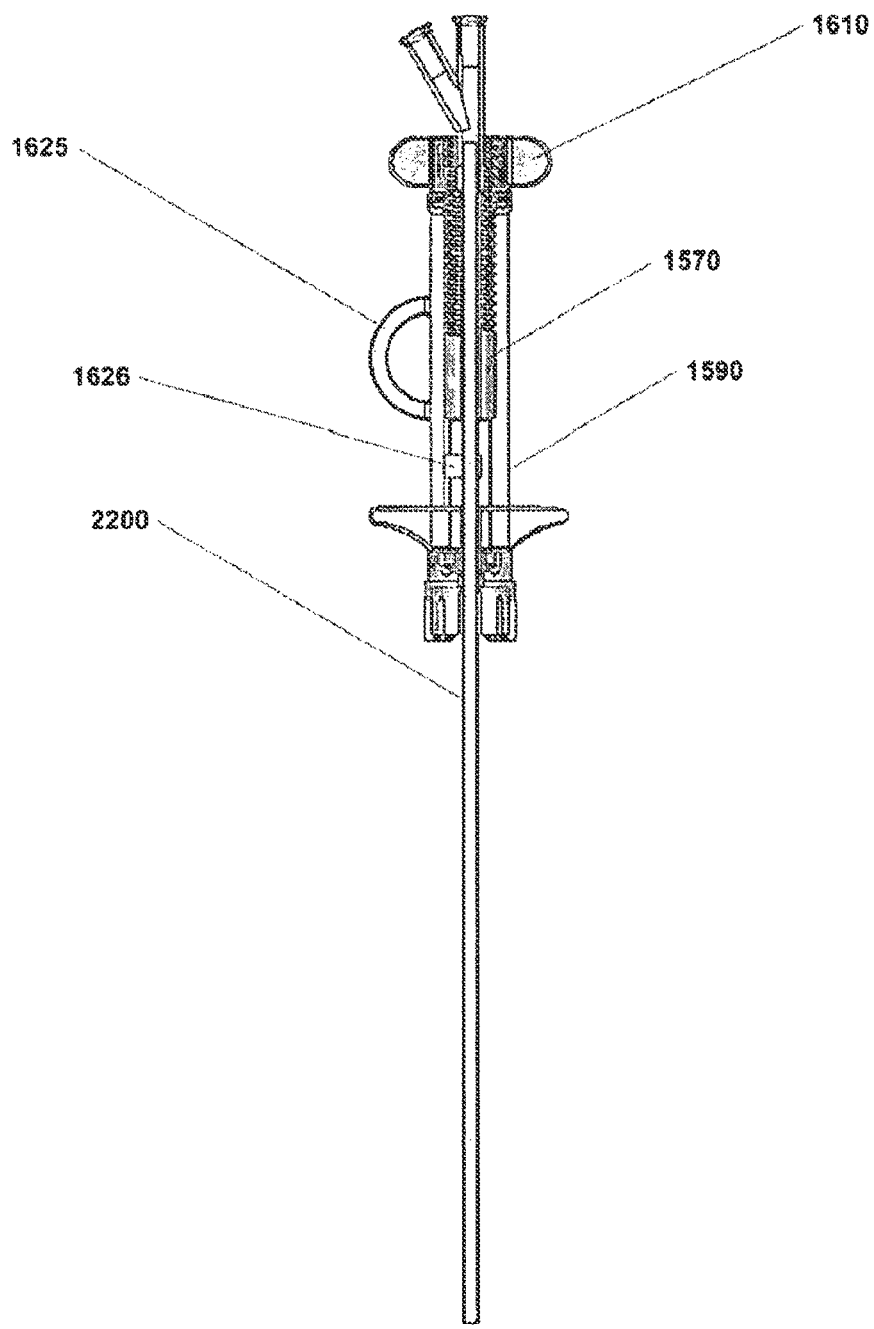
FIG. 16 is a side cross-sectional assembled view of the embodiment of FIG. 15, in combination with a surgical tool.

FIG. 15 is a perspective exploded view of certain components of another embodiment. FIG. 16 is a side cross-sectional assembled view of the same. This embodiment operates generally according to the principles described above and therefore many common components are not illustrated for convenience of description only. In this particular embodiment, extraction collar 1610 attaches to outer sheath 1570 by mating threads as described above. Outer sheath 1570 slides within extraction collar 1590 according to complementary mating features 1570a and 1590a. Sheath advancement/withdrawal mechanism 1625 comprises clip 1626 for fitting onto the selected surgical tool 2200 by extending through slots 1571 and 1591.

The embodiments of the present invention described above are to be regarded in all respects as being illustrative and nonrestrictive. Accordingly, the present invention may be embodied in other specific forms without deviating from the spirit thereof. The present invention is therefore to be limited only the scopes of the following claims.

We claim:
1. A surgical device for inserting a flowable material into a targeted anatomical region, comprising:
an expandable member having a holding portion, the expandable member having a first opening at a first end and a pre-formed closeable second opening at a second end, the first opening and the closeable second opening both in fluid communication with the holding portion;

a closure device configured to releasably fasten the preformed closeable second opening such that the flowable material is inhibited from flowing into the targeted anatomical region from the holding portion when the preformed closeable second opening is substantially closed by the closure device;

a moveable protective sheath positioned proximate the expandable member, the sheath configured to be displaced from a first position in which the sheath is substantially surrounding a majority of the expandable member to a second position in which the sheath is not substantially surrounding a majority of the expandable member; and an extraction assembly coupled to the sheath, the extraction assembly having a first portion and a second portion movably coupled to the first portion of the extraction assembly such that movement of the second portion of the extraction assembly with respect to the first portion of the extraction assembly concurrently moves the sheath and the expandable member in a proximal direction.

2. The surgical device of claim 1, in which the targeted anatomical region is a vertebral body.

3. The surgical device of claim 1, wherein the extraction assembly includes a slide mechanism slidably movable with respect to the first portion of the extraction assembly, the slide mechanism configured to move the sheath from its first position to its second position.

4. The surgical device of claim 1, wherein said expandable member defines a plurality of holes extending therethrough.

5. The surgical device of claim 1, wherein the expandable member includes a flexible wall.

6. The surgical device of claim 1, further comprising an injection port in fluid communication with the holding portion and configured to introduce the flowable material into the holding portion.

7. A surgical device for inserting a flowable material into a vertebral body, comprising:

an expandable member defining an interior lumen, the expandable member having a first opening at a first end and a second opening at a second end, the first opening and the second opening both in fluid communication with the interior lumen;

a closure device configured to releasably fasten the second opening such that the second opening is substantially closed, the flowable material inhibited from flowing from the interior lumen into the vertebral body when the second opening is substantially closed;

a moveable protective sheath positioned proximate the expandable member, the sheath configured to be displaced from a first position in which the sheath substantially surrounds the expandable member to a second position in which a majority of the expandable member extends outward from the sheath; and an extraction assembly having a first portion and a second portion, the first portion of the extraction assembly being disposed about at least a portion of the sheath, the second portion of the extraction assembly being movably coupled to the first portion of the extraction assembly such that movement of the second portion of the extraction assembly with respect to the first portion of the extraction assembly concurrently moves the sheath and the expandable member in a proximal direction.

8. An extractable device for inserting a flowable material into a vertebral body, said device comprising:

a filling member having a flexible wall, a holding portion, an injection port at one end of the holding portion, and a pre-formed opening in fluid communication with the holding portion;

a closure device configured to releasably fasten the pre-formed opening such that the pre-formed opening is substantially closed;

a moveable protective sheath positioned proximate the filling member, the sheath configured to be displaced from a first position in which the sheath substantially surrounds the filling member to a second position in which substantially all of the filling member is not surrounded by the sheath; and an extraction assembly having a first portion and a second portion, the first portion of the extraction assembly being disposed about at least a portion of a proximal end of the sheath, the second portion of the extraction assembly being movably coupled to the first portion of the extraction assembly such that movement of the second portion of the extraction assembly with respect to the first portion of the extraction assembly concurrently moves the sheath and the expandable member in a proximal direction;

the flowable material configured to be introduced into the holding portion via the injection port when the holding portion is disposed within the vertebral body, the flowable material remains within the vertebral body after the holding portion is removed from the vertebral body.

9. The surgical device of claim 7, wherein the sheath is configured to be removed from the vertebral body when the sheath is in the second position.

10. The surgical device of claim 7, wherein at least a portion of the sheath is disposed within the vertebral body when the sheath is in the second position.

11. The surgical device of claim 7, wherein the flowable material is received by the expandable member via the first opening when the sheath is in the second position.

12. The extractable device of claim 8, wherein the flowable material is inhibited from flowing from the holding portion into the vertebral body when the pre-formed opening is substantially closed.

13. The extractable device of claim 8, wherein the holding portion is configured to be removed from the vertebral body with the sheath when the sheath is in the second position.

14. The surgical device of claim 7, wherein, when flowable material is disposed in the interior lumen of the expandable member and the second opening at the second end of the expandable member is open, the second opening at the second end of the expandable member has a first cross-sectional diameter and a portion of the expandable member between its first end and its second end has a second cross-sectional diameter less than the first cross-sectional diameter of the second opening.

15. The surgical device of claim 7, wherein the extraction assembly includes a slide mechanism slidably movable with respect to the first portion of the extraction assembly, the slide mechanism configured to move the sheath from its first position to its second position.

16. The extractable device of claim 8, wherein, when the flowable material has been introduced into the holding portion of the filling member and the pre-formed opening is open, the pre-formed opening of the filling member has a first cross-sectional diameter and a portion of the filling member between its injection port and the pre-formed opening has a second cross-sectional diameter less than the first cross-sectional diameter of the pre-formed opening.

17. The extractable device of claim 8, wherein the extraction assembly includes a slide mechanism slidably movable with respect to the first portion of the extraction assembly, the slide mechanism configured to move the sheath from its first position to its second position.

18. The surgical device of claim 1, wherein at least a portion of the expandable member including the second opening is conically shaped.

19. The surgical device of claim 1, wherein, when the flowable material when flowable material is disposed in the holding portion of the expandable member and the second opening at the second end of the expandable member is open, the second opening at the second end of the expandable member has a first cross-sectional diameter and a portion of the expandable member between its first end and its second end has a second cross-sectional diameter less than the first cross-sectional diameter of the second opening.

20. The surgical device of claim 1, further comprising:
a handle coupleable to the extraction assembly, the handle configured to move the second portion of the extraction assembly with respect to the first portion of the extraction assembly.

\* \* \* \* \*